US007169764B1

(12) United States Patent
Parmacek et al.

(10) Patent No.: US 7,169,764 B1
(45) Date of Patent: *Jan. 30, 2007

(54) PROMOTER FOR SMOOTH MUSCLE CELL EXPRESSION

(75) Inventors: Michael S. Parmacek, Bryn Mawr, PA (US); Julian Solway, Glencoe, IL (US)

(73) Assignee: Arch Development Corporation, Chicago, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/381,750

(22) PCT Filed: Aug. 29, 1997

(86) PCT No.: PCT/US97/16204

§ 371 (c)(1),
(2), (4) Date: Jan. 25, 2001

(87) PCT Pub. No.: WO98/15575

PCT Pub. Date: Apr. 16, 1998

(51) Int. Cl.
*A61K 31/711* (2006.01)
(52) U.S. Cl. .................. 514/44; 435/455; 435/377; 623/1.13; 623/1.41
(58) Field of Classification Search ................ 435/455, 435/375; 514/44; 623/1.13, 1.41
See application file for complete search history.

(56) References Cited

U.S. PATENT DOCUMENTS

| 5,837,534 | A | | 11/1998 | Olson et al. | |
| 6,114,311 | A | * | 9/2000 | Parmacek et al. | ............. 514/44 |
| 6,284,743 | B1 | * | 9/2001 | Parmacek et al. | ............. 514/44 |
| 6,291,211 | B1 | * | 9/2001 | Parmacek et al. | ......... 435/69.1 |
| 6,331,527 | B1 | * | 12/2001 | Parmacek et al. | ............. 514/44 |

FOREIGN PATENT DOCUMENTS

| EP | 666270 A2 | 7/1995 |
| WO | WO 94/11506 | 5/1994 |
| WO | WO 94/13824 | 6/1994 |
| WO | WO 96/00006 | 1/1996 |
| WO | WO 96/26742 | 9/1996 |
| WO | WO 97/35974 | 10/1997 |

OTHER PUBLICATIONS

Chang et al., "Cytostatic gene therapy for vascular proliferative disorders with a constitutively active form of the retinoblastoma gene product," *Science*, 267:518-522, 1995.
Kemp et al., "Cloning and analysis of the promoter region of the rat SM22 alpha gene," ABSTRACT, *Biochem. J.*, 310:1037-1043, 1995.
Li et al., "Expression of the SM22 alpha promoter in transgenic mice provides evidence for distinct transcriptional regulatory programs in vascular and visceral smooth muscle cells," *J. Cell Bio.*, 132(5):849-859, 1996.
Moessler et al., "The Sm22 promoter directs tissue-specific expression in arterial but not venous or visceral smooth muscle cells in transgenic mice," *Development*, 122:2415-2425, 1996.
Solway et al., "Structure and expression of a smooth muscle cell-specific gene, SM22 alpha," ABSTRACT, *J. Biol. Chem.*, 270(22):13460-13469, 1995.
Cserjesi et al., "MHox: a mesodermally restricted homeodomain protein that binds an essential site in the muscle creatine kinase enhancer," *Development*, 115:1087-1101, 1992.
Dalton and Treisman, "Characterization of SAP-1, a Protein Recruited by Serum Response Factor to the c-fos Serum Response Element," *Cell*, 68:597-612, Feb. 1992.
Devlin et al., "Identification of a Muscle-specific Enhancer within the 5'-Flanking Region of the Human Myoglobin Gene," *J. of Biol. Chem.*, 264(23):13896-13901, Aug. 1989.
Dierks et al., "Three Regions Upstream from the Cap Site are Required for Efficient and Accurate Transcription of the Rabbit β-Globin Gene in Mouse 3T6 Cells," *Cell*, 32:695-706, Mar. 1983.
Dynan and Tjian, "The Promoter-Specific Transcription Factor Sp 1 Binds to Upstream Sequences in the SV40 Early Promoter," *Cell*, 35:79-87, Nov. 1983.
Edmondson et al., "Analysis of the Myogenin Promoter Reveals an Indirect Pathway for Positive Autoregulation Mediated by the Muscle-Specific Enhancer Factor MEF-2," *Mol. and Cell. Biol. USA*, 12(9):3665-3677, Sep. 1992.
Evans et al., "An erythrocyte-specific DNA-binding factor recognizes a regulatory sequence common to all chicken globin genes," *Proc. Natl. Acad. Sci.*, 85:5976-5980, Aug. 1988.
Fields and Song, "A novel genetic system to detect protein—protein interactions," *Nature*, 340:245-246, Jul. 1989.
Forrester et al., "A Paradigm for Restenosis Based on Cell Biology: Clues for the Development of New Preventive Therapies," *JACC*, 17(3):758-769, Mar. 1991.
Frid et al., "Myosin Heavy-Chain Isoform Composition and Distribution in Developing and Adult Human Aortic Smooth Muscle," *J. Vasc. Res.*, 30:279-292, 1993.
Gimona et al., "Smooth muscle specific expression of calponin," *FEBS*, 274(1,2):159-162, Nov. 1990.
Gorski et al., "Molecular Cloning of a Diverged Homeobox Gene That is Rapidly Down-Regulated during the $G_0/G_1$ Transition in Vascular Smooth Muscle Cells," *Mol. and Cell. Biol.*, 13(6):3722-3733, Jun. 1993.
Gossett et al., "A New Myocyte-Specific Enhancer-Binding Factor That Recognizes a Conserved Element Associated with Multiple Muscle-Specific Genes.," *Mol. and Cell. Biol.*, 9(11):5022-5033, Nov. 1989.

(Continued)

*Primary Examiner*—James Ketter
(74) *Attorney, Agent, or Firm*—Fulbright & Jaworski LLP

(57) ABSTRACT

Disclosed is a smooth muscle cell specific promoter, the SM22α gene promoter as well as the murine cDNA and genomic SM22α nucleic acid sequences. Also disclosed are methods of preventing restenosis following balloon angioplasty and methods of treating asthma based on inhibition of smooth muscle cell proliferation by expressing cell cycle control genes, or contraction inhibiting peptides in smooth muscle cells, under the control of the SM22α promoter.

12 Claims, 3 Drawing Sheets

OTHER PUBLICATIONS

Gottesdiener et al., "Isolation and Structural Characterization of the Human 4F2 Heavy-Chain Gene, and Inducible Gene Involved in T-Lymphocyte Activation," *Mol. and Cell. Biol.*, 8(9):3809-3819, Sep. 1988.

Grepin et al., "A Hormone-Encoding Gene Identifies a Pathway for Cardiac but Not Skeletal Muscle Gene Transcription," *Mol. and Cell. Biol.*, 14(5):3115-3129, May 1994.

Grueneberg et al., "Human and *Drosophila* Homeodomain Proteins That Enhance the DNA-Binding Activity of Serum Response Factor," *Science*, 257:1089-1095, Aug. 1992.

Gustafson et al., "Interaction of Nuclear Proteins with Muscle-Specific Regulatory Sequences of the Human Cardiac α-Actin Promoter," *Mol. and Cell. Biol.*, 8(10):4110-4119, Oct. 1988.

Gualberto et al., "Functional Antagonism Between YY1 and the Serum Response Factor," *Mol. and Cell. Biol.*, 12(9):4209-4214, Sep. 1992.

Hasty et al., "Muscle deficiency and neonatal death in mice with a targeted mutation in the *myogenin* gene," *Nature*, 364:501-506, Aug. 1993.

Ip et al., "The GATA-4 Transcription Factor Transactivates the Cardiac Muscle-Specific Troponin C Promoter-Enhancer in Nonmuscle Cells," *Mol. and Cell. Biol.*, 14(11):7517-7526, Nov. 1994.

Jones et al., "A Cellular DNA-Binding Protein That Activates Eukaryotic Transcription and DNA Replication," *Cell*, 48:79-89, Jan. 1987.

Jaynes et al., "The Muscle Creatine Kinase Gene is Regulated by Multiple Upstream Elements, Including a Muscle-Specific Enhancer," *Mol. and Cell. Biol.*, 8(1):62-70, Jan. 1988.

Johansen and Prywes, "Serum response factor: transcriptional regulation of genes induced by growth factors and differentiation," *Biochimica et Biophysica Acta*, 1242, 1-10, 1995.

Kadonaga and Tjian, "Affinity purification of sequence-specific DNA binding proteins," *Proc. Natl., Acad. Sci. USA*, 83:5889-5893, Aug. 1986.

Kretsinger, "Structure and Evolution of Calcium-Modulated Proteins," *Critical Reviews in Biochemistry*, CRC Press, 8(1):119-174, Jul. 1980.

Lees-Miller et al., "Isolation and Characterization of an Abundant and Novel 22-kDa Protein (SM22) from Chicken Gizzard Smooth Muscle," *J. of Biol. Chem.*, 262(7):2988-2993, Mar. 1987.

Lee et al., "Displacement of BrdUrd-induced YY1 by serum response factor activates skeletal α-actin transcription in embryonic myoblasts," *Proc. Natl. Acad. Sci.USA*, 89:9814-9818, Oct. 1992.

Lilly et al., "Requirement of MADS Domain Transcription Factor D-MEF2 for Muscle Formation in *Drosophila*," *Science*, 267:688-693, Feb. 1995.

Martin, et al., "The paired-like homeo box gene *MHox* is required for early events of skeletogenesis in multiple lineages," *Genes & Development*, 9:1237-1249, 1995.

Lassar et al., "MyoD is a Sequence-Specific DNA Binding Protein Requiring a Region of myc Homology to Bind to the Muscle Creatine Kinase Enhancer," *Cell*, 58:823-831, Sep. 1989.

Liu et al., "Restenosis After Coronary Angioplasty, Potential Biologic Determinants and Role of Intimal Hyperplasia," *Circulation*, 79(6):1374-1387, Jun. 1989.

Miano et al., "Smooth Muscle Myosin Heavy Chain Exclusively Marks the Smooth Muscle Lineage During Mouse Embryogenesis," *Circulation Research*, 75(5):803-812, Nov. 1994.

Min et al., "The 5'-Flanking Region of the Mouse Vascular Smooth Muscle α-Actin Gene Contains Evolutionarily Conserved Sequence Motifs within a Functional Promoter," *J. of Biol. Chem.*, 265(27):16667-16675, Sep. 1990.

Minty and Kedes, "Upstream Regions of the Human Cardiac Actin Gene That Modulate its Transcription in Muscle Cells: Presence of an Evolutionarily Conserved Repeated Motif," *Mol. and Cell. Biol.*, 6(6):2125-2136, Jun. 1986.

Mitchell et al., "Positive and Negative Regulation of Transcription *In Vitro*: Enhancer-Binding Protein AP-2 is Inhibited by SV40 T Antigen," *Cell*, 50:847-861, Sep. 1987.

Natesan and Gilman, "DNA bending and orientation-dependent function of YY1 in the c-fos promoter," *Genes & Development*, 7:2497-2509, 1993.

Nishida et al., "cDNA cloning and mRNA expression of calponin and SM22 in rat aorta smooth muscle cells," *Gene*, 130:297-302, 1993.

Olson, "MyoD family: a paradigm for development?", *Genes & Development*, 4:1454-1461, 1990.

Orkin, "GATA-Binding Transcription Factors in Hematopoietic Cells," *Blood*, 80(3):575-581, Aug. 1992.

Owens et al., "Expression of Smooth Muscle-specific α-Isoactin in Cultured Vascular Smooth Muscle Cells: Relationship between Growth and Cytodifferentiation," *J. of Cell Biol.*, 102:343-352, Feb. 1986.

Parmacek et al., "A Novel Myogenic Regulatory Circuit Controls Slow/Cardiac Troponin C Gene Transcription in Skeletal Muscle," *Mol. and Cell. Biol.*, 14(3):1870-1885, Mar. 1994.

Parmacek et al., "Identification and Characterization of a Cardiac-Specific Transcriptional Regulatory Element in the Slow/Cardiac Troponin C Gene," *Mol. and Cell. Biol.*, 12(5):1967-1976, May 1992.

Parmacek et al., "The Structure and Regulation of Expression of the Murine Fast Skeletal Troponin C Gene," *J. of Biol. Chem.*, 265(26):15970-15976, Sep. 1990.

Parmacek and Leiden, "Structure and Expression of the Murine Slow/Cardiac Troponin C Gene," *J. of Biol. Chem.*, 264(22):13217-13225, Aug. 1989.

Ross, "The pathogenesis of atherosclerosis: a perspective for the 1990s," *Nature*, 362:801-809, Apr. 1993.

Ross, "Atherosclerosis: A Defense Mechanism Gone Awry," *American J. of Pathology*, 143(4):872-1002, Oct. 1993.

Ross, "The Pathogenesis of Atherosclerosis—An Update," *The New England Journal of Medicine*, 314(8):488-500, Feb. 1986.

Rovner, et al., "Expression of Smooth Muscle and Nonmuscle Myosin Heavy Chains in Cultured Vascular Smooth Muscle Cells," *J. of Biol. Chem.*, 261(31):14740-14745, Nov. 1986.

Rudnicki et al., "MyoD or Myf-5 is Required for the Formation of Skeletal Muscle," *Cell*, 75:1351-1359, Dec. 1993.

Sawtell and Lessard, Cellular Distribution of Smooth Muscle Actins during Mammalian Embryogenesis: Expression of the α-Vascular but not the γ-Enteric Isoform in Differentiating Striated Myocytes, *J. of Cell Biol.*, 109(6, pt. 1):2929-2937, Dec. 1989.

Schwartz et al., "Replication of Smooth Muscle Cells in Vascular Disease," *Circulation Research*, 58(4):427-444, Apr. 1986.

Shanahan et al., "Isolation of Gene Markers of Differentiated and Proliferating Vascular Smooth Muscle Cells," *Circulation Research*, 73(1):193-204, Jul. 1993.

Schwartz et al., "The Restenosis Paradigm Revisited: An Alternative Proposal for Cellular Mechanisms," *JACC*, 20(5):1284-1293, Nov. 1992.

Singh et al., "Molecular Cloning of an Enhancer Binding Protein: Isolation by Screening of an Expression Library with a Recognition Site DNA," *Cell*, 52:415-423, Feb. 1988.

Tapscott and Weintraub, "MyoD and the Regulation of Myogenesis by Helix-Loop-Helix Proteins," *J. Clin. Invest.*, 87:1133-1138, Apr. 1991.

Ueki et al., "Expression of high and low molecular weight caldesmons during phenotypic modulation of smooth muscle cells," *Proc. Natl., Acad. Sci.USA*, 84:9049-9053, Dec. 1987.

Wilkie and Simon, "Cloning Multigene Families with Degenerate PCR Primers," *Methods: A Companion to Methods in Enzymology*, 2(1):32-41, Feb. 1991.

Zanellato et al., "Myosin Isoform Expression and Smooth Muscle Cell Heterogeneity in Normal and Atherosclerotic Rabbit Aorta," *Arteriosclerosis*, 10(6):996-1009, Nov./Dec. 1990.

Aikawa et al., "Human Smooth Muscle Myosin Heavy Chain Isoforms as Molecular Markers for Vascular Development and Atherosclerosis," *Circulation Research*, 73(6):1000-1012, Dec. 1993.

Akira et al., "A nuclear factor for IL-6 expression (NF-IL6) is a member of a C/EBP family," *The EMBO Journal*, 9(6):1897-1906, 1990.

Blank et al., "Elements of the Smooth Muscle α-Action Promoter Required *in Cis* for Transcriptional Activation in Smooth Muscle," *J. of Biol. Chem.*, 267(2):984-989, Jan. 1992.

Carroll et al., "Structure and Complete Nucleotide Sequence of the Chicken α-Smooth Muscle (Aortic) Actin Gene," *J. of Biol. Chem.*, 261(19):8965-8976, Jul. 1986.

\* cited by examiner

SEQUENCE LISTING

<160> NUMBER OF SEQ ID NOS: 51

<210> SEQ ID NO 1
<211> LENGTH: 1419
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 1
gaattcagga cgtaatcagt ggctggaaag caagagctct agaggagctc cagcttatta      60
tgacccttcc ttcagatgcc acaaggaggt gctggagttc tatgcaccaa tagcttaaac     120
cagccaggct ggctgtagtg gattgagcgt ctgaggctgc acctctctgg cctgcagcca     180
gttctgggtg agactgaccc tgcctgaggg ttctctcctt ccctctctct actcctttct     240
ccctctccct ctccctctct ctgtttcctg aggtttccag gattggggat gggactcaga     300
gacaccacta aagccttacc ttttaagaag ttgcattcag tgagtgtgtg agacatagca     360
cagatagggg cagaggagag ctggttctgt ctccactgtg tttggtcttg ggtactgaac     420
tcagaccatc aggtgtgata gcagttgtct ttaaccctaa ccctgagcct gtctcacctg     480

-continued

```
tcccttccca agaccactga agctaggtgc aagataagtg gggacccttt ctgaggtggt      540
aggatctttc acgataagga ctattttgaa gggagggagg gtgacactgt cctagtcctc      600
ttaccctagt gtctccagcc ttgccaggcc ttaaacatcc gcccattgtc accgctctag      660
aaggggccag ggttgacttg ctgctaaaca aggcactccc tagagaagca cccgctagaa      720
gcataccata cctgtgggca ggatgaccca tgttctgcca cgcacttggt agccttggaa      780
aggccacttt gaacctcaat tttctcaact gttaaatggg gtggtaactg ctatctcata      840
ataaagggga acgtgaaagg aaggcgtttg catagtgcct ggttgtgcag ccaggctgca      900
gtcaagacta gttcccacca actcgatttt aaagccttgc aagaaggtgg cttgtttgtc      960
ccttgcaggt tcctttgtcg ggccaaactc tagaatgcct ccccctttct ttctcattga     1020
agagcagacc caagtccggg taacaaggaa gggtttcagg gtcctgccca taaaaggttt     1080
ttcccggccg ccctcagcac cgccccgccc gacccccgc agcatctcca aagcatgcag      1140
agaatgtctc cggctgcccc cgacagactg ctccaacttg gtgtctttcc ccaaatatgg     1200
agcctgtgtg gagtgagtgg ggcggcccgg ggtggtgagc caagcagact tccatgggca     1260
gggaggggcg ccagcggacg gcagaggggt gacatcactg cctaggcggc ctttaaaccc     1320
ctcacccagc cggcgcccca gcccgtctgc cccagcccag acaccgaagc tactctcctt     1380
ccagtccaca aacgaccaag ccttgtaagt gcaagtcat                            1419

<210> SEQ ID NO 2
<211> LENGTH: 991
<212> TYPE: DNA
<213> ORGANISM: Artificial Sequence
<220> FEATURE:
<221> NAME/KEY: CDS
<222> LOCATION: (38)..(217)
<220> FEATURE:
<221> NAME/KEY: CDS
<222> LOCATION: (322)..(447)
<220> FEATURE:
<221> NAME/KEY: CDS
<222> LOCATION: (866)..(967)
<220> FEATURE:
<223> OTHER INFORMATION: Description of Artificial Sequence: Synthetic
      Primer

<400> SEQUENCE: 2
cttttctcca cactctatac tttagctctg cctcaac atg gcc aac aag ggt cca       55
                                        Met Ala Asn Lys Gly Pro
                                          1               5 tcc tac ggc atg agc cga gaa gtg cag tcc aaa att gag aag aag tat      103
Ser Tyr Gly Met Ser Arg Glu Val Gln Ser Lys Ile Glu Lys Lys Tyr
            10                  15                  20 gac gag gag ctg gag gag cga cta gtg gag tgg att gta gtg cag tgt      151
Asp Glu Glu Leu Glu Glu Arg Leu Val Glu Trp Ile Val Val Gln Cys
        25                  30                  35 ggc cct gat gta ggc cgc cca gat cgt ggg cgc ctg ggc ttc cag gtg      199
Gly Pro Asp Val Gly Arg Pro Asp Arg Gly Arg Leu Gly Phe Gln Val
    40                  45                  50 tgg ctg aag aat ggt gtg gtgagtaacc cttgcgaagg gaatctaggg              247
Trp Leu Lys Asn Gly Val
55                  60 atgtgtatgc cgccctacaa actgtgagac agactccctg agctgagtgt tcagttgtgt     307
tctgtacctg gcag att ctg agc aaa ttg gtg aac agc ctg tat cct gag       357
         Ile Leu Ser Lys Leu Val Asn Ser Leu Tyr Pro Glu
                65                  70
```

-continued

```
gga tcg aag cca gtg aag gtg cct gag aac cca ccc tcc atg gtc ttt        405
Gly Ser Lys Pro Val Lys Val Pro Glu Asn Pro Pro Ser Met Val Phe
        75                  80                  85 aag cag atg gaa cag gtg gct caa ttc ttg aag gca gct gaa                447
Lys Gln Met Glu Gln Val Ala Gln Phe Leu Lys Ala Ala Glu
        90                  95                 100 gattatggag tcatcaagac tgacatgttc cagactgttg acctctatga aggtataagg      507
aaaaaagggc tggagccagt gggcgagtgg agagcaagat tatcagtcaa ggagaaggaa      567
tatcaaaagc cacaaccagc tctgttgatg tgttcatagc aggaatggga tatgccaaga      627
gaacacatag caagggacc agcttggtgg tacagcattt ccttctgggt acaagggcct       687
gttttggatc ctagaatatc aaatatatac cacaccatac tcactagggt ttagaatatg      747
gtctcttgaa ccctcttgat ttggtgccac ttgctccttg gttggaccat ttttgaagct      807
gggcaggtat tgcctatatg gtcctgaaat tagctccctg gccactcttc tcataggt       865 aag gat atg gca gca gtg cag agg act cta atg gct ttg ggc agt ttg        913
Lys Asp Met Ala Ala Val Gln Arg Thr Leu Met Ala Leu Gly Ser Leu
       105                 110                 115 gct gtg acc aaa aac gat gga aac tac cgt gga gat ccc aac tgg ttt        961
Ala Val Thr Lys Asn Asp Gly Asn Tyr Arg Gly Asp Pro Asn Trp Phe
       120                 125                 130 atg aag tatgtgtcca ctgggtctct ctgt                                     991
Met Lys
135
```

<210> SEQ ID NO 3
<211> LENGTH: 60
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 3

```
Met Ala Asn Lys Gly Pro Ser Tyr Gly Met Ser Arg Glu Val Gln Ser
  1               5                  10                  15

Lys Ile Glu Lys Lys Tyr Asp Glu Glu Leu Glu Glu Arg Leu Val Glu
             20                  25                  30

Trp Ile Val Val Gln Cys Gly Pro Asp Val Gly Arg Pro Asp Arg Gly
         35                  40                  45

Arg Leu Gly Phe Gln Val Trp Leu Lys Asn Gly Val
     50                  55                  60
```

<210> SEQ ID NO 4
<211> LENGTH: 42
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 4

```
Ile Leu Ser Lys Leu Val Asn Ser Leu Tyr Pro Glu Gly Ser Lys Pro
  1               5                  10                  15

Val Lys Val Pro Glu Asn Pro Pro Ser Met Val Phe Lys Gln Met Glu
             20                  25                  30

Gln Val Ala Gln Phe Leu Lys Ala Ala Glu
         35                  40
```

<210> SEQ ID NO 5

```
<211> LENGTH: 34
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 5

Lys Asp Met Ala Ala Val Gln Arg Thr Leu Met Ala Leu Gly Ser Leu
 1               5                  10                  15

Ala Val Thr Lys Asn Asp Gly Asn Tyr Arg Gly Asp Pro Asn Trp Phe
            20                  25                  30

Met Lys

<210> SEQ ID NO 6
<211> LENGTH: 575
<212> TYPE: DNA
<213> ORGANISM: Artificial Sequence
<220> FEATURE:
<221> NAME/KEY: CDS
<222> LOCATION: (28)..(168)
<220> FEATURE:
<223> OTHER INFORMATION: Description of Artificial Sequence:  Synthetic
      Primer

<400> SEQUENCE: 6
acttaccctg gttccttttc ttctagg aaa gcc cag gag cat aag agg gac ttc     54
                              Lys Ala Gln Glu His Lys Arg Asp Phe
                                1               5 aca gac agc caa ctg cag gag ggg aag cac gtc att ggc ctt caa atg     102
Thr Asp Ser Gln Leu Gln Glu Gly Lys His Val Ile Gly Leu Gln Met
 10              15                  20                  25 ggc agc aac aga gga gcc tcg cag gct ggc atg aca ggc tat ggg cga     150
Gly Ser Asn Arg Gly Ala Ser Gln Ala Gly Met Thr Gly Tyr Gly Arg
            30                  35                  40 ccc cgg cag atc atc agt tagaaaggga aggccagccc tgagctgcag            198
Pro Arg Gln Ile Ile Ser
            45 catcctgctt agcctgcctc acaaatgcct atgtaggttc ttagccctga cagctctgag   258 gtgtcactgg gcaaagatga ctgcacatgg gcagctccca cctatcctta gcctcagccc   318 agcatcttac cccagagcca ccactgccct ggccctgtt cccagctgta cccccacctc    378 tactgttcct ctcatcctgg agtaagcagg gagaagtggg ctggggtagc tggctgtagg   438 ccagcccact gtccttgata tcgaatgtcc tttgaaggag acccagccca gcctctacat   498 cttttcctgg aatatgtttt tgggttgaaa ttcaaaaagg aaaaagaaa aatatataaa    558 tatatatata tatatac                                                  575

<210> SEQ ID NO 7
<211> LENGTH: 47
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 7

Lys Ala Gln Glu His Lys Arg Asp Phe Thr Asp Ser Gln Leu Gln Glu
 1               5                  10                  15

Gly Lys His Val Ile Gly Leu Gln Met Gly Ser Asn Arg Gly Ala Ser
            20                  25                  30

Gln Ala Gly Met Thr Gly Tyr Gly Arg Pro Arg Gln Ile Ile Ser
```

<210> SEQ ID NO 8
<211> LENGTH: 1102
<212> TYPE: DNA
<213> ORGANISM: Artificial Sequence
<220> FEATURE:
<221> NAME/KEY: CDS
<222> LOCATION: (77)..(679)
<220> FEATURE:
<223> OTHER INFORMATION: Description of Artificial Sequence: Synthetic Primer

<400> SEQUENCE: 8

```
gcccgtctgc cccagcccag acaccgaagc tactctcctt ccagtccaca aacgaccaag        60
ccttctctgc ctcaac atg gcc aac aag ggt cca tcc tac ggc atg agc cga       112
                  Met Ala Asn Lys Gly Pro Ser Tyr Gly Met Ser Arg
                    1               5                  10 gaa gtg cag tcc aaa att gag aag aag tat gac gag gag ctg gag gag        160
Glu Val Gln Ser Lys Ile Glu Lys Lys Tyr Asp Glu Glu Leu Glu Glu
             15                  20                  25 cga cta gtg gag tgg att gta gtg cag tgt ggc cct gat gta ggc cgc        208
Arg Leu Val Glu Trp Ile Val Val Gln Cys Gly Pro Asp Val Gly Arg
 30                  35                  40 cca gat cgt ggg cgc ctg ggc ttc cag gtg tgg ctg aag aat ggt gtg        256
Pro Asp Arg Gly Arg Leu Gly Phe Gln Val Trp Leu Lys Asn Gly Val
 45                  50                  55                  60 att ctg agc aaa ttg gtg aac agc ctg tat cct gag gga tcg aag cca        304
Ile Leu Ser Lys Leu Val Asn Ser Leu Tyr Pro Glu Gly Ser Lys Pro
                 65                  70                  75 gtg aag gtg cct gag aac cca ccc tcc atg gtc ttt aag cag atg gaa        352
Val Lys Val Pro Glu Asn Pro Pro Ser Met Val Phe Lys Gln Met Glu
             80                  85                  90 cag gtg gct caa ttc ttg aag gca gct gaa gat tat gga gtc atc aag        400
Gln Val Ala Gln Phe Leu Lys Ala Ala Glu Asp Tyr Gly Val Ile Lys
         95                 100                 105 act gac atg ttc cag act gtt gac ctc tat gaa ggt aag gat atg gca        448
Thr Asp Met Phe Gln Thr Val Asp Leu Tyr Glu Gly Lys Asp Met Ala
110                 115                 120 gca gtg cag agg act cta atg gct ttg ggc agt ttg gct gtg acc aaa        496
Ala Val Gln Arg Thr Leu Met Ala Leu Gly Ser Leu Ala Val Thr Lys
125                 130                 135                 140 aac gat gga aac tac cgt gga gat ccc aac tgg ttt atg aag aaa gcc        544
Asn Asp Gly Asn Tyr Arg Gly Asp Pro Asn Trp Phe Met Lys Lys Ala
                145                 150                 155 cag gag cat aag agg gac ttc aca gac agc caa ctg cag gag ggg aag        592
Gln Glu His Lys Arg Asp Phe Thr Asp Ser Gln Leu Gln Glu Gly Lys
            160                 165                 170 cac gtc att ggc ctt caa atg ggc agc aac aga gga gcc tcg cag gct        640
His Val Ile Gly Leu Gln Met Gly Ser Asn Arg Gly Ala Ser Gln Ala
        175                 180                 185 ggc atg aca ggc tat ggg cga ccc cgg cag atc atc agt tagaaaggga        689
Gly Met Thr Gly Tyr Gly Arg Pro Arg Gln Ile Ile Ser
    190                 195                 200 aggccagccc tgagctgcag catcctgctt agcctgcctc acaaatgcct atgtaggttc       749
ttagccctga cagctctgag gtgtcactgg gcaaagatga ctgcacatgg gcagctccca       809
cctatcctta gcctcagccc agcatcttac cccagagcca ccactgccct ggcccctgtt       869
cccagctgta cccccacctc tactgttcct ctcatcctgg agtaagcagg gagaagtggg       929
ctggggtagc tggctgtagg ccagcccact gtccttgata tcgaatgtcc tttgaaggag       989
```
acccagccca gcctctacat cttttcctgg aatatgtttt tgggttgaaa ttcaaaaagg    1049
aaaaaagaaa aatatataaa tatatatata tacaaaaaaa aaaaaaaaaa aaa          1102

<210> SEQ ID NO 9
<211> LENGTH: 201
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 9

Met Ala Asn Lys Gly Pro Ser Tyr Gly Met Ser Arg Glu Val Gln Ser
1               5                   10                  15

Lys Ile Glu Lys Lys Tyr Asp Glu Glu Leu Glu Arg Leu Val Glu
            20                  25                  30

Trp Ile Val Val Gln Cys Gly Pro Asp Val Gly Arg Pro Asp Arg Gly
        35                  40                  45

Arg Leu Gly Phe Gln Val Trp Leu Lys Asn Gly Val Ile Leu Ser Lys
    50                  55                  60

Leu Val Asn Ser Leu Tyr Pro Glu Gly Ser Lys Pro Val Lys Val Pro
65                  70                  75                  80

Glu Asn Pro Pro Ser Met Val Phe Lys Gln Met Glu Gln Val Ala Gln
                85                  90                  95

Phe Leu Lys Ala Ala Glu Asp Tyr Gly Val Ile Lys Thr Asp Met Phe
            100                 105                 110

Gln Thr Val Asp Leu Tyr Glu Gly Lys Asp Met Ala Ala Val Gln Arg
        115                 120                 125

Thr Leu Met Ala Leu Gly Ser Leu Ala Val Thr Lys Asn Asp Gly Asn
    130                 135                 140

Tyr Arg Gly Asp Pro Asn Trp Phe Met Lys Lys Ala Gln Glu His Lys
145                 150                 155                 160

Arg Asp Phe Thr Asp Ser Gln Leu Gln Glu Gly Lys His Val Ile Gly
                165                 170                 175

Leu Gln Met Gly Ser Asn Arg Gly Ala Ser Gln Ala Gly Met Thr Gly
            180                 185                 190

Tyr Gly Arg Pro Arg Gln Ile Ile Ser
        195                 200

<210> SEQ ID NO 10
<211> LENGTH: 43
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 10
atcgaattcc gctactctcc ttccagccca caaacgacca agc                     43

<210> SEQ ID NO 11
<211> LENGTH: 33
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 11

```
atcaagcttg gtgggagctg cccatgtgca gtc                         33
```

<210> SEQ ID NO 12
<211> LENGTH: 25
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 12

```
tgccgtagga tggacccttg ttggc                                  25
```

<210> SEQ ID NO 13
<211> LENGTH: 10
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 13

```
ytawaaatar                                                   10
```

<210> SEQ ID NO 14
<211> LENGTH: 10
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 14

```
tttaaaatcg                                                   10
```

<210> SEQ ID NO 15
<211> LENGTH: 10
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 15

```
ttcaaaatag                                                   10
```

<210> SEQ ID NO 16
<211> LENGTH: 8
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 16

Cys Cys Cys Met Asn Ser Ser Ser
  1               5

<210> SEQ ID NO 17
<211> LENGTH: 9
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 17

```
Lys Arg Gly Gly Cys Lys Arg Arg Lys
 1               5
```

<210> SEQ ID NO 18
<211> LENGTH: 9
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 18

```
Thr Lys Asn Asn Gly Asn Ala Ala Lys
 1               5
```

<210> SEQ ID NO 19
<211> LENGTH: 8
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 19

```
Met Ile Arg Ile Cys Arg Lys Lys
 1               5
```

<210> SEQ ID NO 20
<211> LENGTH: 381
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 20

```
agtcaagact agttcccacc aactcgattt taaagccttg caagaaggtg gcttgtttgt      60
cccttgcagg ttcctttgtc gggccaaact ctagaatgcc tcccccttc tttctcattg     120 aagagcagac ccaagtccgg gtaacaagga agggtttcag ggtcctgccc ataaaaggtt    180
tttcccggcc gccctcagca ccgccccgcc ccgaccccg cagcatctcc aaagcatgca     240
gagaatgtct ccggctgccc ccgacagact gctccaactt ggtgtctttc cccaaatatg    300
gagcctgtgt ggagtgagtg gggcggcccg gggtggtgag ccaagcagac ttccatgggc    360
agggaggggc gccagcggac g                                              381
```

<210> SEQ ID NO 21
<211> LENGTH: 47
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 21

```
aaggaagggt ttcagggtcc tgcccataaa aggttttcc cggccgc                    47
```

<210> SEQ ID NO 22
<211> LENGTH: 47
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 22
aaggaagggt tcagggtcc tgcccataga tcttttttcc cggccgc    47

<210> SEQ ID NO 23
<211> LENGTH: 43
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 23 ccgcccctcag caccgccccg ccccgaggcc cgcagcatgt ccg    43

<210> SEQ ID NO 24
<211> LENGTH: 43
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 24 ccgcccctcag caccgcggat ccccgacccc cgcagcatct ccg    43

<210> SEQ ID NO 25
<211> LENGTH: 37
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 25
ctccaaagca tgcagagaat gtctccggct gcccccg    37

<210> SEQ ID NO 26
<211> LENGTH: 37
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 26
ctcggatcca tgctagcaat gaattcggct gcccccg    37

<210> SEQ ID NO 27
<211> LENGTH: 44
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 27
tccaacttgg tgtctttccc caaatatgga gcctgtgtgg agtg    44

<210> SEQ ID NO 28
<211> LENGTH: 44
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 28
tccaacttgg tgtctttccc caaggatcca gcctgtgtgg agtg                            44

<210> SEQ ID NO 29
<211> LENGTH: 44
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 29
tccaacttgg tgtctttccc cggatatgga gcctgtgtgg agtg                            44

<210> SEQ ID NO 30
<211> LENGTH: 44
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 30
tccaacttgg tgtctttccc caaattagga gcctgtgtgg agtg                            44

<210> SEQ ID NO 31
<211> LENGTH: 21
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 31
gggcagggag gggcgccagc g                                                    21

<210> SEQ ID NO 32
<211> LENGTH: 21
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 32
gggcaggtac cgaattcagc g                                                    21

<210> SEQ ID NO 33
<211> LENGTH: 37
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 33
ggacggcaga ggggtgacat cactgcctag gcggccg                                   37

<210> SEQ ID NO 34
<211> LENGTH: 37
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 34
ggacggcaga ggggatccat gcctgcctag gcggccg                                   37

-continued

<210> SEQ ID NO 35
<211> LENGTH: 37
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 35
ggacggcaga ggggatccat cactgcctag gcggccg                              37

<210> SEQ ID NO 36
<211> LENGTH: 29
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 36
ctggctaaag gggcggggct tggccagcc                                       29

<210> SEQ ID NO 37
<211> LENGTH: 26
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 37
ctcccatttc catgacgtca tggtta                                          26

<210> SEQ ID NO 38
<211> LENGTH: 47
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 38
aaggaagggt ttcagggtcc tgcccataga tcttttttcc cggccgc                   47

<210> SEQ ID NO 39
<211> LENGTH: 43
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 39
ccgccctcag caccgcggat ccccgacccc cgcagcatct ccg                       43

<210> SEQ ID NO 40
<211> LENGTH: 37
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 40
ctcggatcca tgctagcaat gaattcggct gccccg                               37

<210> SEQ ID NO 41
<211> LENGTH: 44
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 41
tccaacttgg tgtctttccc caaggatcca gcctgtgtgg agtg                     44

<210> SEQ ID NO 42
<211> LENGTH: 44
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 42
tccaacttgg tgtctttccc cggatatgga gcctgtgtgg agtg                     44

<210> SEQ ID NO 43
<211> LENGTH: 44
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 43
tccaacttgg tgtctttccc caaattagga gcctgtgtgg agtg                     44

<210> SEQ ID NO 44
<211> LENGTH: 21
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 44
gggcaggtac cgaattcagc g                                              21

<210> SEQ ID NO 45
<211> LENGTH: 37
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 45
ggacggcaga ggggatccat gcctgcctag gcggccg                             37

<210> SEQ ID NO 46
<211> LENGTH: 37
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 46
ggacggcaga ggggatccat cactgcctag gcggccg                             37

```
<210> SEQ ID NO 47
<211> LENGTH: 10
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 47 ccwwwwwwcc                                                            10

<210> SEQ ID NO 48
<211> LENGTH: 45
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 48
ctccaacttg gtgtctttcc ccggatatgg agcctgtgtg gagtg                     45

<210> SEQ ID NO 49
<211> LENGTH: 45
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 49
ctccaacttg gtgtctttcc ccaaattagg agcctgtgtg gagtg                     45

<210> SEQ ID NO 50
<211> LENGTH: 10
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 50
ccaaatatgg                                                            10

<210> SEQ ID NO 51
<211> LENGTH: 10
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 51
ccatatatgg                                                            10
```

PROMOTER FOR SMOOTH MUSCLE CELL EXPRESSION

The government owns rights in the present invention pursuant to grant numbers R01-HL48257, U01 AI34566 and R01HL51145 from the Public Health Service.

This application is a national phase application under 35 U.S.C. § 371 of International Application No. PCT/US97/16204 filed Aug. 29, 1997, which claims priority to U.S. patent application Ser. No. 08/726,807, filed Oct. 7, 1996, now U.S. Pat. No. 6,090,618, which claims priority to U.S. Application Ser. No. 60/004,868, filed on Oct. 5, 1995, now abandoned.

BACKGROUND OF THE INVENTION

The present invention relates generally to the fields of gene expression, particularly tissue specific expression, and more particularly smooth muscle cell specific expression. The invention also relates to cell proliferation diseases such as atherosclerosis, restenosis following balloon angioplasty and airway blockage in asthma.

The phenotypic plasticity of smooth muscle cells (SMCs) permits this muscle cell lineage to subserve diverse functions in multiple tissues including the arterial wall, uterus, respiratory, urinary and digestive tracts. In contrast to fast and slow skeletal muscle cells which fuse and terminally differentiate before expressing contractile protein isoforms, SMCs are capable of simultaneously proliferating and expressing a set of lineage-restricted proteins including myofibrillar isoforms, cell surface receptors and SMC-restricted enzymes. Moreover, in response to specific physiological and pathophysiological stimuli, SMCs can modulate their phenotype by down-regulating a set of contractile protein genes, and in so doing, convert from the so called "contractile phenotype" to a de-differentiated "secretory phenotype" (Mosse et al., *Lab Invest.*, 53:556–562, 1985; Owens et al., *J. Cell Biol.*, 102:343–352, 1986; Rovner et al., *J. Biol. Chem.*, 261:14740–14745, 1986; Taubman et al., *J. Cell Biol.*, 104:1505–1513, 1987; Ueki et al., *Proc. Natl. Acad. Sci. USA*, 84:9049–9053, 1987; Belkin et al., *J. Biol. Chem.*, 263:6631–6635, 1988; Glukhova et al., *Proc. Natl. Acad. Sci. USA*, 85:9542–9546, 1988; Chaponnier et al., *Eur. J. Biochem.*, 190:559–565, 1990; Gimona et al., *FEBS Letters*, 274: 159–162, 1990; Shanahan et al., *Circ. Res.*, 73:193–204, 1993).

This phenotypic modulation has been implicated in the pathogenesis of a number of disease states including atherosclerosis and restenosis following coronary balloon angioplasty (Ross, *N. Engl. J. Med.* 314:488–500, 1986; Schwartz et al., *Circ. Res.*, 58:427–440, 1986; Zanellato et al., *Arteriosclerosis*, 10:996–1009, 1990; Ross, *Am. J. Pathol.*, 43:987–1002, 1993; Olson and Klein, *Genes Dev.*, 8:1–8, 1994) and may also contribute to the airway remodeling seen in asthma (James et al., *Am. Rev. Respir. Dis.*, 139:242–246, 1989). Restenosis following coronary balloon angioplasty is a major problem, and contributes to the 40% failure rate of this procedure (Schwartz et al., 1992; Liu et al., *Circ.* 79:1374–1387, 1989). Restenosis occurs because the smooth muscle cells are stimulated to proliferate after angioplasty and thus block the arterial wall. Because of restenosis, balloon angioplasty is used mainly for palliation in patients who are not acceptable candidates for open heart surgery (*Scientific American Medicine*, Rubenstein and Federman, Eds., March 1993, Section 1, XII, page 11). A method is needed, therefore, to control or inhibit the proliferation of smooth muscle cells after angioplasty.

Although RDAd efficiently transduce both resting and proliferating SMCs in vivo, a potential limitation of their use in the clinical setting is their capacity to infect and program transgene expression in many different cell lineages and tissues (Ohno et al., *Science*, 265 (5173):781–784, 1994; Haddada et al., *Current Topics in Microbiology & Immunolog,.* 199 (Pt 3):297–306, 1995). For example, localized arterial administration of RDAd results in efficient infection of endothelial cells, vascular SMCs and adventitial cells (French et al., *Circulation*, 90 (5):2402–2413, 1994; Simari et al., *J. Clin. Invest.*, 98 (1):225–235, 1996). Moreover, intravenous administration of these vectors results in high-level gene transfer to the liver and lung (Kashyap et al., *J. Clin. Invest.* 96 (3):1612–1620, 1995; Johns et al., *J. Clin. Invest.* 96 (2):1152–1158, 1995; Miller and Vile, *FASEB Journal*, 9 (2):190–199, 1995). Several approaches have been used in an attempt to circumvent this problem. First, it has been possible to restrict the expression of a viral transgene to a specific cell or tissue by administering the virus ex vivo. However, this approach is laborious and is not practical for the treatment of most vascular proliferative disorders. A second approach has involved delivery of adenoviral particles locally within the vasculature (to the site of vessel wall injury) or within a tissue (Ohno et al., 1994; Chang et al., *Science*, 267:518–522, 1995a; Guzman et al., 1994; Chang et al., *Mol. Medicine*, 1:172–181, 1995b). Specially-modified catheter delivery systems including coated-balloons and intravascular stents have been designed in order to achieve high local concentrations of adenovirus within the vasculature (March et al., *Human Gene Therapy*, 6 (1):41–53, 1995; Rajasubramanian et al., *ASAIO Journal*, 40 (3):M584–M589, 1994; Kito et al., *ASAIO Journal*, 40 (3):M260–M266, 1994). However, the usefulness of these approaches may be limited within the human coronary circulation due to the high frequency of side branches. Moreover, such catheter delivery systems do not restrict transgene expression to specific cell types in the vessel wall. Finally, several groups have reported that the tissue-tropism of RDAd can be modified by electrostatically conjugating adenoviral proteins to ligands that can bind specifically to tissue-specific cell-surface receptors (Krasnykh et al., *Journal of Virology*, 70 (10):6839–6846, 1996). This approach has been used to successfully target RDAd to hepatocytes and hematopoietic progenitor cell lines (Schwarzenberger et al., *Blood*, 87 (2):472–478, 1996).

The use of tissue-specific transcriptional regulatory elements represents an alternative strategy to restrict adenoviral transgene expression to specific cell lineages or tissues in vivo (Miller and Vile, 1995). While theoretically appealing, this strategy is potentially limited because the adenovirus genome contains multiple highly active transcriptional enhancers that are capable of transactivating a variety of different promoters in multiple cell lineages (Haddada et al., 1995). Such a targeting strategy is particularly problematic in smooth muscle cells because of the lack of smooth muscle cell-specific transcriptional regulatory elements that function in vivo. Thus, there is still a need for discovery of a smooth muscle cell specific promoter that is not expressed in other types of cells and is constitutively expressed in both quiescent and proliferating cells and that maintains its tissue specificity when administered to an animal.

SUMMARY OF THE INVENTION

The present invention seeks to overcome these and other drawbacks in the prior art by providing a promoter that is capable of expression of a heterologous gene in a tissue specific manner, in particular, smooth muscle cells, and by offering the further advantage that the control of expression directed by the promoter is constitutive and cell cycle independent. The promoter of the present invention thus promotes transcription in both resting and proliferating cells, in contrast to other known smooth muscle cell promoters that are down-regulated in proliferating cells. This promoter may be used therefore, to express heterologous proteins or mRNAs in proliferating smooth muscle cells and to control proliferative diseases or to promote angiogenesis, for example.

The invention may be described, in certain embodiments, as an isolated nucleic acid segment comprising an SM22α promoter sequence operatively linked to a heterologous gene and capable of directing expression of that gene. The isolated SM22α promoter may be described as the region immediately upstream of the transcriptional start site of the murine SM22α gene. As described herein a nucleic acid segment having a sequence according to bases 899–1382 of SEQ ID NO:1, is also effective to promote transcription in a smooth muscle cell and a nucleic acid segment having that sequence or the transcriptional control elements of that sequence would also fall within the scope of the claimed invention. Such homologous promoters may be isolated from an animal sequence, such as from a mouse, pig, rat, hamster, rabbit or even a human genome or cDNA library using any of the sequences disclosed herein as a molecular probe. In addition, based on the present disclosure, one of skill might construct such a promoter by splicing elements taken from various sources including, but not limited to, chemically synthesized nucleic acid molecules, or elements removed from other naturally occurring promoters, or from the SM22α promoter. It is understood that any such promoter, or a promoter having the essential elements of the promoter disclosed herein and useful to express a heterolgous nucleic acid sequence would be encompassed by the spirit and scope of the invention claimed herein.

The promoter region of the present invention may be defined as comprising that region of the genome immediately upstream (5') of the structural SM22α gene, and controlling expression of that gene. For example, the promoter may comprise the region of up to 30, 40, 50, 100, 500, 1,000, 1,500, 2,000 or even up to 5,000 bases directly upstream of the transcriptional start site of the SM22α gene, and more specifically, an SM22α promoter of the present invention may be described as an isolated nucleic acid segment that comprises a contiguous sequence of bases 1–1381 (−1338 to +41) of SEQ ID NO:1. The designations of −1338 to +41 and the like indicate the position of a base relative to the transcriptional start site (+1), which, in the murine genome, is disclosed herein to be base 1341 of SEQ ID NO:1. The promoter of the present invention may also be described as an isolated nucleic acid segment that comprises a contiguous sequence of bases 899–1381 (−441 to +41) of SEQ ID NO:1. Certain elements of the promoter that are identified in light of the present disclosure are a TATA box 29-bp 5' of the start site, five consensus E boxes/bHLH myogenic transcription factor binding sites located at bps −534, −577, −865, −898, −910, and −1267, three consensus GATA-4 binding sites located at bps −504, −828, −976, two AT-rich, potential MEF-2/rSRF binding sites located at bps −407 and −770 and at least one cis-acting, positive transcriptional regulatory element contained by bp −435 to −416. In addition, the promoter of the present invention contains consensus CArG/SRF binding sites located at bps −150 and −273 and one CACC box located at bp −104.

Thus, the promoter of the present invention may comprise some or all of the elements described in the previous paragraph. Such elements may be isolated and recombined by techniques well known in the art to produce a smooth muscle cell specific promoter that may be smaller than the 441 to 482 bases disclosed herein as a minimal sequence required for constitutive smooth muscle cell transcription. It is also known that certain stretches of sequence in the promoter are required for spacing of the cis acting elements and that any sequence that does not impart hairpin loops or other deleterious structural properties may be substituted for those regions so long as the spacing and conformation remains the same. It is understood that all such promoters would be encompassed by the present invention.

The isolated nucleic acid segments of the present invention may also be defined as comprising a nucleic acid sequence or even a gene operatively linked to an isolated SM22α promoter sequence. Operatively linked is understood to mean that the gene is joined to the promoter region such that the promoter is oriented 5' to the gene and is of an appropriate distance from the transcription start site, so that the transcription of the gene will be dependent on or controlled by the promoter sequence. The arts of restriction enzyme digestion and nucleic acid ligation to be used in construction of a promoter-gene construct are well known in the art as exemplified by Maniatis et al., *Molecular Cloning, A Laboratory Manual*, Cold Spring Harbor, N.Y., 1982, (incorporated herein by reference). Therefore one would, using standard techniques, prepare a gene by restriction enzyme digestion to have a compatible end sequence, or even a blunt end, to be ligated downstream of the SM22α promoter. The restriction enzyme recognition site may be a naturally occurring sequence, or a sequence generated by site directed mutagenesis, by a PCR™ primer sequence or by any other means known in the art. Alternatively, one might chemically synthesize a gene or gene fragment or an oligonucleotide containing an appropriate restriction enzyme recognition sequence or one might prepare a gene by any of several methods known in the art.

The gene or nucleic acid segment may be, for example, a structural gene that encodes a full length protein, a portion or part of a protein, or a peptide that one desires to express in a smooth muscle cell. The gene may also encode an RNA sequence, such as an antisense oligonucleotide sequence, or even a regulatory sequence that affects the expression of another gene or genes. In certain preferred embodiments of the invention, the gene will be a cell cycle control gene, such as a retinoblastoma (Rb) gene, a phosphorylation deficient Rb gene, p53, p21, p16, p27, a cell cycle dependent kinase inhibitor, E2F inhibitor, a CDK kinase or a cyclin gene; alternatively the gene will be an angiogenesis gene such as VEGF, iNOS, eNOS, basic FGF or FGF-5, or the gene may be a cytotoxic gene such as a herpes simplex thymidine kinase gene, or any other gene, the expression of which will affect proliferation of the smooth muscle cells in which the gene is expressed, and/or endothelial cells in such a ways as to effect the growth of new blood vessels. Alternatively, the nucleic acid segment may encode an antisense RNA effective to inhibit expression of a cell cycle control gene or regulatory element. Antisense constructs are oligo- or polynucleotides comprising complementary nucleotides to the control regions or coding segments of a DNA molecule, such as a gene or cDNA. Such constructs may include antisense versions of both the promoter and other control regions, exons, introns and exon:intron boundaries of a gene. Antisense molecules are designed to inhibit the transcription, translation or both, of a given gene or construct, such that the levels of the resultant protein product are reduced or diminished. Antisense RNA constructs, or DNA encoding such antisense RNAs, may be employed to inhibit gene transcription or translation or both within a host cell, either in vitro or in vivo, such as within a host animal, including a human subject. Of course, the antisense constructs have evident utility in the types of nucleic acid hybridization described herein. The gene may also encode an antigenic sequence and the necessary leader sequence for transport to the cell surface, or it may encode an enzyme, or an intracellular signal protein or peptide, or it may even encode an SM22α gene or SM22α cDNA gene. Particularly preferred is a constitutively active form of the Rb gene product that inhibits cellular proliferation, disclosed in Chang et al., 1995a (incorporated herein by reference).

The present invention may also be described, in certain embodiments, as a recombinant vector that is capable of replication in an appropriate host cell and that comprises an SM22α promoter sequence as disclosed herein, including an SM22α promoter operatively linked to a gene or nucleic acid segment. Preferred vectors include, but are not limited to, a plasmid, a raus sarcoma virus (RSV) vector, a p21 viral vector, an adeno-associated viral vector or an adenoviral vector. In addition, a variety of viral vectors, such as retroviral vectors, herpes simplex virus (U.S. Pat. No. 5,288,641, incorporated herein by reference), cytomegalovirus, and the like may be employed, as described by Miller (*Microbiol. Immunol.*, 158:1, 1992, incorporated herein by reference). Recombinant adeno-associated virus (AAV) and AAV vectors may also be employed, such as those described in U.S. Pat. No. 5,139,941, incorporated herein by reference. Recombinant adenoviral vectors are currently preferred. Techniques for preparing replication-defective infective viruses are well known in the art, as exemplified by Ghosh-Choudhury & Graham, *Biochem. Biophys. Res. Comm.*, 147:964–973 (1987); McGrory et al., *Virology*, 163:614–617, (1988); and Gluzman et al., *In: Eukaryotic Viral Vectors* (Gluzman, Y., Ed.) pp. 187–192, Cold Spring Harbor Press, Cold Spring Harbor, N.Y., (1982), each incorporated herein by reference. Also preferred are plasmid vectors designed for increased expression such as those described in Tripathy et al., *Proc. Natl. Acad. Sci. USA*, 93:10876–80, 1996.

A preferred adenovirus used in the practice of the present invention is replication-defective and particularly those that lack the early gene region E1 or the early gene regions E1 and E3. For example, the foreign DNA of interest, such as the smooth muscle specific transcriptional regulatory sequence of the present invention may be inserted into the region of the deleted E1 and E3 regions of the adenoviral genome. In this way, the entire sequence is capable of being packaged into virions that can transfer the foreign DNA into an infectable host cell. A preferred adenovirus is a type 5 adenovirus and a SM22α promoter and coding sequence are preferably flanked by adenovirus type 5 sequences.

The invention may be described in certain embodiments as a replication deficient adenoviral vector, wherein the vector comprises a smooth muscle cell specific transcriptional regulatory segment. Preferred smooth muscle cell specific transcriptional regulatory segments include, but are not limited to an SM22α promoter, a smooth muscle calponin promoter, a smooth muscle myosin heavy chain promoter, a smooth muscle alpha actin promoter, a smooth muscle alpha actin enhancer, a telokin promoter, a smooth muscle gamma-actin promoter or a smooth muscle gamma-actin enhancer. In addition, the enhancer elements may be included in an adenoviral vector of the present invention in combination with a promoter segment. A smooth muscle cell specific transcriptional regulatory segment of the present invention may be isolated from any source such as a mammal or a bird, for example, and including but not limited to a mouse, pig, rat, rabbit, human or chicken. Specific examples of such segments would include a mouse smooth muscle calponin promoter (bases 1–1216 of Genbank accession #U38929, or the promoter sequence of Genbank accession #U37071, or bases 1–631 of Genbank accession #L49022); a smooth muscle myosin heavy chain promoter from a mouse (bases 1–1536 of Genbank accession # U53469), a rat (bases 1–1699 of Genbank accession #U55179, or bases 1–2425 of Genbank accession #U83321), or a rabbit (bases 1–2267 of Genbank accession #U15514); a human smooth muscle alpha actin promoter (bases 1–1746 of Genbank accession #D00618, or bases 1–892 of Genbank accession #J05193) or a human smooth muscle alpha actin enhancer (bases 1789–5559 of Genbank accession #D00618); a chicken smooth muscle alpha actin promoter (bases 1-1013 of Genbank accession #M13756, D00041, N00041), a mouse smooth muscle alpha actin promoter (bases 1–1074 of Genbank accession #M57409, M35194), a rat smooth muscle alpha actin promoter (Genbank accession #S76011); a rabbit telokin promoter (bases 1–3460 of Genbank accession #U40712); a mouse smooth muscle gamma-actin promoter (bases 1–1076 of Genbank accession #U19488) or a mouse smooth muscle gamma-actin enhancer (bases 1123–5703 of Genbank accession #U19488). (All sequences discussed in this paragraph incorporated herein by reference).

The smooth muscle cell specific regulatory element or segment may be operatively linked to a gene or nucleic acid segment as defined above, i.e. it may be a cell cycle control gene, such as a retinoblastoma (Rb) gene, a phosphorylation deficient Rb gene, p53, p21, p16, p27, a cell cycle dependent kinase inhibitor, E2F inhibitor, a CDK kinase or a cyclin gene; alternatively the gene will be an angiogenesis gene such as VEGF, iNOS, eNOS, basic FGF or FGF-5, or the gene may be a cytotoxic gene such as a herpes simplex thymidine kinase gene.

In certain embodiments of the invention, the vector of the present invention is dispersed in a pharmaceutically or pharmacologically acceptable solution. Preferred solutions include neutral saline solutions buffered with phosphate, lactate, Tris, and the like. Of course, one will desire to purify the vector sufficiently to render it essentially free of undesirable contaminant, such as defective interfering adenovirus particles or endotoxins and other pyrogens such that it will not cause any untoward reactions in the individual receiving the vector construct. A preferred means of purifying the vector involves the use of buoyant density gradients, such as cesium chloride gradient centrifugation.

The present invention may also be described, in certain embodiments, as a method of expressing a gene in a smooth muscle cell comprising the steps of: obtaining an isolated nucleic acid segment comprising a gene operatively linked to an SM22α promoter region; transferring that nucleic acid segment into a smooth muscle cell; and maintaining the smooth muscle cell under conditions effective to express the gene. In this method of the invention, the SM22α promoter region preferably includes bases −441 to +41 of the SM22α gene (899–1382 of SEQ ID NO:1) or even bases −441 to +1 of the murine SM22α gene (899–1341 of SEQ ID NO:1) and may include up to 5,000 bases of the SM22α promoter. In the practice of this method, the heterologous gene is preferably a reporter gene, a cell cycle control regulatory gene, an angiogenesis gene, a virally encoded gene such as herpes simplex virus thymidine kinase (Chang, et. al., 1995b), an antisense molecule, or it may encode a muscle contraction inhibiting peptide, and may encode an Rb gene product or a peptide having the sequence MIRICRKK, SEQ ID NO:19, or any gene or obvious variant of any gene as described above. The Rb gene may be the wild type Rb gene or it may be an altered gene such that the gene product is phosphorylation deficient. It is apparent from the present disclosure that it may not be necessary to collect the gene product in the practice of the present method. For example, if the gene product is a cell cycle regulatory element, or a contraction inhibiting peptide, then the cell itself will be the target of that effect and the utility of the method will not depend on collecting or even on identifying a protein product. However, certain gene products will have utility as markers of gene expression and as useful proteins or peptides produced by a recombinant cell.

In addition, the present invention may be described as a method of inhibiting smooth muscle cell proliferation comprising the steps of: obtaining an isolated nucleic acid segment comprising a cell cycle regulatory gene operatively linked to an SM22α promoter region; transferring the nucleic acid segment into a smooth muscle cell to obtain a transfected cell; and maintaining the smooth muscle cell under conditions effective to express the cell cycle regulatory gene; wherein expression of the cell cycle regulatory gene inhibits proliferation of the smooth muscle cell. In the practice of the method, the cell cycle regulatory gene operatively linked to an SM22α promoter region may comprise a viral vector, a plasmid vector or it may comprise an adenoviral vector. Further, the cell cycle regulatory gene may preferably encode Rb, a phosphorylation deficient Rb gene, p53, p21, p16, p27, a cell cycle dependent kinase inhibitor, E2F inhibitor, a CDK kinase or a cyclin gene, for example.

The present invention may also be described in certain broad aspects as a method of preventing restenosis in a subject following balloon angioplasty of either a coronary artery, renal artery, peripheral artery or carotid artery, for example. In addition, the present invention may be described in certain broad embodiments as a method of preventing restenosis in a subject following balloon angioplasty of a vein as would be used in a coronary artery bypass surgery, or other bioprosthetic grafts that might be used in the periphery. This method comprises the steps of obtaining a viral vector comprising a cell cycle regulatory gene operatively linked to an SM22α promoter region dispersed in a pharmaceutically acceptable solution and administering the solution to the subject. The subject may be an animal subject and is preferably a human subject. In the practice of the method, the viral vector is preferably a replication defective adenoviral vector and the gene may preferably encode herpes simplex thymidine kinase, p53, Rb, a phosphorylation deficient Rb gene, p53, p21, p16, p27, a cell cycle dependent kinase inhibitor, E2F inhibitor, a CDK kinase or a cyclin gene.

An aspect of the invention is also a method of screening for identifying smooth muscle cell specific transcriptional control elements and particularly those elements that work in trans. The method as provided herein preferably employs a reporter gene that confers on its recombinant hosts a readily detectable phenotype that is either expressed or inhibited, as the case may be. Generally reporter genes encode (a) a polypeptide not otherwise produced by the host cell; or (b) a protein or factor produced by the host cell but at lower levels; or (c) a mutant form of a polypeptide produced by the host cell. Preferably the gene encodes an enzyme which produces colorimetric or fluorometric change in the host cell which is detectable by in situ analysis and which is a quantitative or semi-quantitative function of transcriptional activation. Exemplary enzymes include esterases, phosphatases, proteases (tissue plasminogen activator or urokinase) and other enzymes capable of being detected by activity that generates a chromophore or a fluorophore as will be known to those of skill in the art.

Examples of such a reporter gene are the *E. coli* β-galactosidase (β-gal) and firefly luciferase genes. The β-gal enzyme produces a color change upon cleavage of the indigogenic substrate, indolyl-β-D-galactoside by cells expressing β-galactosidase. Thus, this enzyme facilitates automatic plate reader analysis of expression directly in microtiter wells containing transformants treated with candidate activators. Also, since the endogenous β-galactosidase activity in mammalian cells ordinarily is quite low, the analytic screening system using β-galactosidase is not hampered by host cell background. This enzyme offers the further advantage that expression can be monitored in vivo by tissue analysis as described below.

Another class of reporter genes that confers detectable characteristics on a host cell are those that encode polypeptides, generally enzymes, that render their transformants resistant against toxins, e.g., the neo gene, which protects host cells against toxic levels of the antibiotic G418; a gene encoding dihydrofolate reductase, which confers resistance to methotrexate, or the chloramphenicol acetyltransferase (CAT) gene. Other genes for use in the screening assay herein are those capable of transforming hosts to express unique cell surface antigens, e.g. viral env proteins such as HIV gp120 or herpes gD, which are readily detectable by immunoassays.

In certain embodiments, the present invention may be described as a recombinant vector comprising an isolated SM22α promoter positioned adjacent a gene in a position to control expression of the gene. The splicing of nucleic acid sequences is well known in the art as described above and the insertion of such genes into vectors is also well known in the art. The vector of the present invention may be a plasmid, a phagemid, a replication defective adenovirus, an adeno-associated virus or a retrovirus, for example. The type of vector does not necessarily in and of itself define the present invention, and therefore in certain embodiments, any vector that can transfer genetic material into a cell to be expressed in that cell will be useful in the present invention. It is also understood that the nucleic acid segments may be transferred into a cell by means such as liposomes, receptor ligand carriers, mechanical means such as electroporation, etc. and that all such embodiments are encompassed within the claimed invention.

However, the recombinant vector of the present invention preferably is a replication deficient adenovirus or a high expression plasmid comprising an SM22α promoter operatively joined to a gene, and wherein the gene may be a cell cycle control gene, such as a retinoblastoma (Rb) gene, a phosphorylationdeficient Rb gene, p53, p21, p16, p27, a cell cycle dependent kinase inhibitor, E2F inhibitor, a CDK kinase or a cyclin gene; alternatively the gene may be an angiogenesis gene such as VEGF, iNOS, eNOS, basic FGF or FGF-5; or the gene may be a cytotoxic gene such as a herpes simplex thymidine kinase gene.

It is understood that the method of inhibiting muscle contraction will have utility in the treatment of palliation of a variety of diseases that arise from muscle cell contraction. Such diseases include, but are not limited to Prinzmetal's angina, hypertension, Raynaud's phenomenon, migraine headache, a variety of collagen vascular diseases such as ELS, scleroderma, pulmonary hypertension, coronary arterial vasospasm, in contractile disorders of smooth muscle cells in the eye, gut, uterus, bladder, spleen, etc., or even in striated muscle spasms in paralysis victims.

In a certain broad aspect the present invention may be described as a method of promoting angiogenesis in a subject comprising the steps of obtaining a nucleic acid segment comprising an angiogenesis factor gene operatively linked to an SM22α promoter region; and transferring the nucleic acid segment into a smooth muscle cell to obtain a transfected cell; wherein expression of the nucleic acid segment in the smooth muscle cell promotes angiogenesis. In the practice of the method, the smooth muscle cell may be a coronary arterial or venous smooth muscle cell, or it may be a peripheral arterial or venous smooth muscle cell. A preferred angiogenesis factor is VEGF, iNOS, eNOS, basic FGF or FGF-5. In certain embodiments of the method, the nucleic acid segment comprising an angiogenesis factor gene operatively linked to an SM22α promoter region is contained in a viral or plasmid vector and the vector is administered to a subject. In certain alternate embodiments the transferring is done ex vivo and the method further comprises the steps of seeding a bioprosthetic graft or stent with the transfected cells to obtain a seeded graft or stent; and placing the seeded graft or stent into a coronary or peripheral artery or vein of a subject.

The present invention may also be described in certain broad aspects as a method of inhibiting smooth muscle proliferation comprising the steps of obtaining a nucleic acid segment comprising a cell cycle regulatory gene operatively linked to an SM22α promoter region; transferring the nucleic acid segment into a primary smooth muscle cell in vivo or ex vivo to obtain a transfected cell; seeding a bioprosthetic graft or stent with the transfected cell to obtain a seeded graft or stent; and placing the seeded graft or stent into a coronary or peripheral artery or vein of a subject, wherein expression of the cell cycle regulatory gene inhibits proliferation of a smooth muscle cell.

The GenBank accession number for the murine SM22α cDNA is L41154. The GenBank accession number for the murine SM22α gene is L41161.

DETAILED DESCRIPTION OF THE PREFERRED EMBODIMENTS

Figure 1:
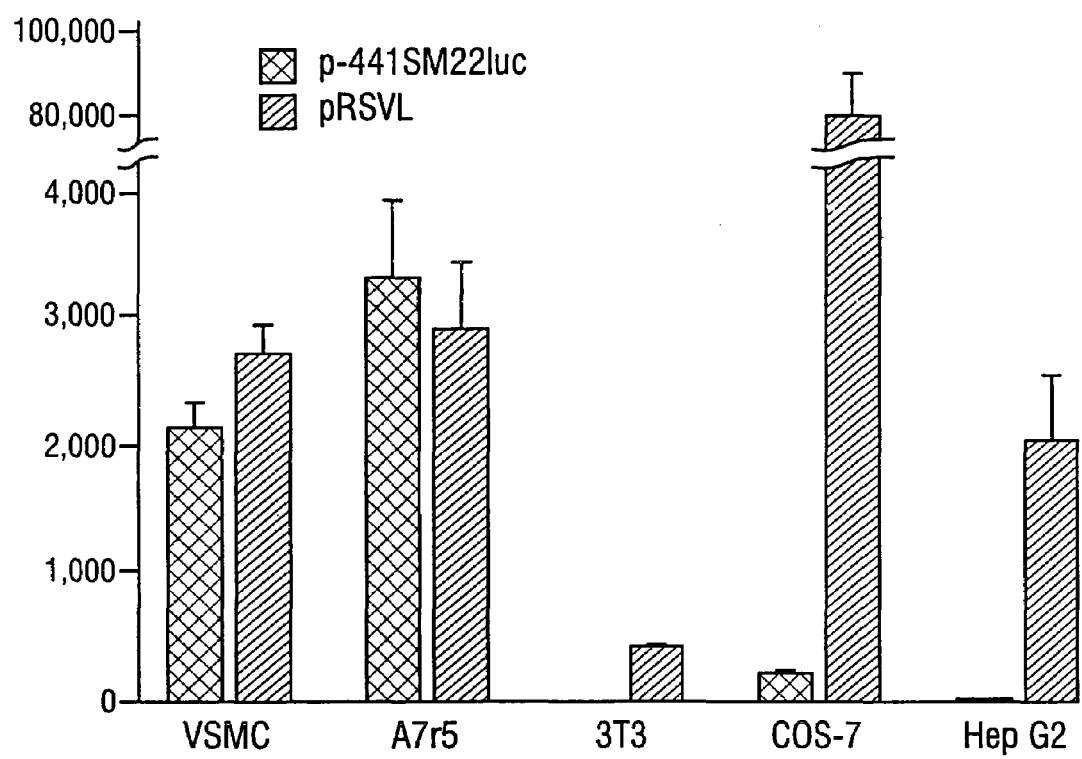
FIG. 1 Cellular-specificity of the 441-bp SM22α promoter. The p-441SM22luc (black bar) and pRSVL (hatched bar) plasmids were transiently transfected into primary rat aortic SMCs (VSMC), A7r5, NIH 3T3 (3T3), COS-7, and Hep G2 cells and the normalized luciferase activities for each respective plasmid was determined. Data are expressed as normalized luciferase light units ±S.E.M.

The present invention arises from the isolation and characterization of a smooth muscle cell specific promoter region that, in its naturally occurring state, controls the expression of the SM22α gene, and the discovery that this isolated promoter region may be operatively joined to a heterologous structural gene and will control the expression of that gene specifically in smooth muscle cells and other myogenic cell lineages including an embryonic skeletal muscle cell. An important element of the present invention is that, unlike other known smooth muscle cell promoters, the SM22α promoter is cell cycle independent and is thus not down-regulated when the cell enters the proliferative state. The promoter sequence of the present invention will be useful in the expression of heterologous genes in a smooth muscle cell, in the discovery of trans and cis acting transcriptional control elements that affect smooth muscle cell gene expression and as a probe to isolate SM22α genes and promoters. In particular, the present invention will find use in the prevention of restenosis following balloon angioplasty or other arterial injury, in the treatment of artherosclerosis or peripheral vascular occlusive disease, in the promotion of angiogenesis in graft or stent implants and in the treatment or prevention of asthma, among other smooth muscle cell proliferative diseases.

As an embodiment of the present invention, a recombinant replication-defective adenoviral vector (RDAd) was generated, designated AdSM22-lacZ, which contains the bacterial lacZ reporter gene under the transcriptional control of the SMC-specific SM22α promoter (Solway et al., *J. Biol. Chem.*, 270 (22): 13460–13469, 1995; Kim et al., *Mol. Cell. Biol.*, (17):2266–2278, 1997; Li et al., *J. Cell Biol.*, 132:

849–859, 1996b). As shown herein, this adenoviral construct, AdSM22-lacZ, programs SMC-specific expression of the lacZ reporter gene in cultured cells. In addition, the SMC-specificity of the AdSM22-lacZ virus is maintained in vivo following intra-arterial, intra-muscular and intravenous administration. Finally, AdSM22-lacZ programs transgene expression in visceral, as well as vascular SMCs in vivo.

It is an important discovery, as disclosed herein, that the expression of a recombinant gene product encoded by a RDAd can be regulated in a cell-lineage restricted fashion by a transcriptional regulatory element in normal cells in vivo. The present inventors have previously generated adenoviral vectors containing other cell lineage-specific transcriptional regulatory elements and observed that the majority of these elements lose their cell lineage-specificity when tested in vivo in the context of an adenoviral vector. Similarly, Arbuthnot et. al. reported that RDAd containing transgenes under the transcriptional control of the alpha-fetoprotein (AFP) promoter are capable of mediating cell lineage-restricted gene expression in hepatoma cells, but not in normal liver parenchyma (Arbuthnot et al., *Human Gene Therapy,* 7 (13):1503–1514, 1996). Without restricting the present invention to any particular theory, it is possible that the murine SM22α promoter may contain an insulator element or a locus control region that is capable of protecting it from the activity of cryptic transcriptional regulatory elements located within the adenoviral genome. In this regard, the murine SM22α promoter is as active as the most potent viral LTRs in SMCs (Solway et al., 1995), and functions in a SMC-specific fashion both in vitro and in transgenic mice in vivo (Kim et al., 1997; Li et al., 1996b; Moessler et al., *Development,* 122:2415–2425, 1996). It is contemplated, therefore, that an insulator element, when isolated from an SM22α promoter will be useful as a means of conferring tissue specificity to those tissue specific promoters that lose tissue specificity when expressed from an adenoviral vector.

Furthermore, in transgenic mice the SM22α promoter is active in arterial, but not visceral SMCs (Li et al., *Circ. Res.,* 78:188–195, 1996a; Kim et al., 1997). Therefore, the demonstration described herein that the lacZ reporter gene encoded by AdSM22-lacZ was expressed in visceral, as well as, vascular SMCs was somewhat surprising. Again, without relying on any particular theory, this difference may reflect the fact that in adenovirus-infected cells DNA remains episomal, whereas, in transgenic mice it is integrated into the host genome where its transcriptional activity can be-modulated by alterations in chromatin structure.

RDAd are particularly useful tools for studying the molecular pathogenesis of atherosclerosis and other vascular proliferative disorders. Adenoviruses can be delivered in spatially- and temporally-restricted fashions to the vessel wall in both normal and atherosclerotic vessels in large and small animals (French et al, 1994; Simari et al., 1996). However, previous studies using these vectors to investigate the pathogenesis of vascular proliferative disorders have not been able to distinguish effects due to alterations in vascular SMC gene expression from those resulting from transgene expression in endothelial or adventitial cells. In this respect, RDAd-containing transgenes under the control of the SM22α promoter allow one to determine directly the effects of SMC-specific transgene expression on vascular SMC proliferation and neointima formation. In addition, because SM22α containing RDAd program transgene expression in visceral SMCs, these viruses may also be useful to examine the pathogenesis and treatment of diseases mediated by visceral SMCs. Examples of such diseases include asthma, achalasia, leiomyosarcomas, irritable bowel syndrome and uterine leiomyomas.

Although the efficacy of RDAd have been established in both large and small animal models of vascular proliferative disease (Ohno et al., 1994; Chang et al., 1995a; Guzman et al., 1994; Yang et al., *Proc. Natl. Acad. Sci. USA,* 93 (15):7905–7910, 1996; Chang et al., 1995b), safety concerns persist due to the capacity of these viruses to infect most cells and tissues. In this regard, SM22α promoter-driven adenoviruses may prove advantageous as vehicles to deliver therapeutic genes to the vessel wall for the treatment of vascular proliferative disorders. The lack of cytotoxic or cytostatic transgene expression in the endothelial cells at the margins of the arterial injury should, in theory, promote more rapid re-endothelialization of the injured vessel by facilitating the proliferation and migration of adjacent endothelial cells (Ohno et al., 1994). Of equal importance, the potential for systemic toxicity resulting from ectopic expression of potentially toxic adenovirus-encoded transgenes in other tissues and organs should be reduced by use of the SMC-specific SM22α promoter. Finally, recent reports have demonstrated that much of the immunogenicity of adenovirus infected cells is due to cellular and humoral immune responses directed against foreign transgene proteins (Kashyap et al., 1995). By restricting ectopic expression of adenovirus-encoded transgenes in non-SMC containing tissues, AdSM22 viruses may also reduce the immune-mediated damage to organs such as the liver and the lung following intentional or inadvertent systemic administration of the vector, as indicated by the finding of decreased hepatic toxicity following IV administration of high dose AdSM22-lacZ.

In one aspect, the present invention provides a process of directing and regulating gene expression in a smooth muscle cell. In accordance with that process, a gene operatively joined to an SM22α promoter is delivered to a smooth muscle cell and the smooth muscle cell is then maintained under physiological conditions and for a period of time sufficient for the gene to enter the smooth muscle cell, for the gene to be transcribed and in certain embodiments, for the product of that gene to be expressed. Delivery is preferably by transfection with a plasmid or a high expression plasmid, replication defective adenovirus, adeno-associated virus, p21 virus, raus sarcoma virus, or other virus vector construct capable of transfecting a smooth muscle cell, and comprising an SM22α promoter operatively joined to a coding sequence that encodes the gene product.

The use of adenovirus as a vector for cell transfection is well known in the art. Adenovirus vector-mediated cell transfection has been reported for various cells (Stratford-Perricaudet, et al., *J. Clin. Invest,* 90, 626–630, 1992). An adenovirus vector of the present invention is replication defective. A virus is rendered replication defective by deletion of the viral early region 1 (E1) region. An adenovirus lacking an E1 region is competent to replicate only in cells, such as human 293 cells, which express adenovirus early region 1 genes from their cellular genome. Thus, such an adenovirus cannot replicate in cells that do not provide the early gene product of the E1 region. In a preferred embodiment, an adenovirus vector used in the present invention is lacking both the E1 and the E3 early gene regions. Thus, it is most convenient to introduce the coding sequence for a gene product at the position from which the E1 and/or E3 coding sequences have been removed (Karlsson et al., *EMBO J.,* 5, 2377–2385, 1986). Preferably, the E1 region of adenovirus is replaced by the coding DNA sequence or gene.

However, the position of insertion within the adenovirus sequences is not critical to the present invention. Techniques for preparing such replication defective adenoviruses are well known in the art as exemplified by Ghosh-Choudhury et al., 1987; McGrory et al., 1988; and Gluzman et al., 1982.

A wide variety of adenovirus vectors can be used in the practice of the present invention. An adenovirus vector can be of any of the 42 different known serotypes of subgroups A–F. Adenovirus type 5 of subgroup C is the preferred starting material for production of a replication-defective adenovirus vector. Adenovirus type 5 is a human adenovirus about which a great deal of biochemical and genetic information is known, and it has historically been used for most constructions employing adenovirus as a vector.

In order to replicate the virus, the vector is co-transfected into 293 cells together with a plasmid carrying the complete adenovirus type 5 genome. Preferred plasmids may also confer ampicillin and tetracycline resistance due to insertion of the appropriate sequences into the virus genome. The molecular strategy employed to produce recombinant adenovirus is based upon the fact that, due to the packaging limit of adenovirus, the plasmid cannot efficiently form plaques on its own. Therefore, homologous recombination between the desired construct and the co-transfected plasmid within a transfected cell results in a viable virus that can be packaged and form plaques only on 293 cells.

Co-transfection is performed in accordance with standard procedures well known in the art. By way of example, 293 cells are cultured in Dulbecco's modified Eagle's medium containing 10% fetal calf serum in a humidified 5% $CO_2$ atmosphere. Confluent 10 cm dishes are split into three 6 cm dishes. On the following day, the cells are cotransfected in calcium phosphate with HeLa DNA as carrier. Six hours after addition of the DNA to the cells, a 15% glycerol stock is used to boost transfection efficiency and the cells are overlaid with 0.65% Noble agar in DMEM containing 2% FCS, 50 mg/ml penicillin G, 10 mg/ml streptomycin sulfate, and 0.25 mg/ml fungizone (GIBCO, Grand Island, N.Y.). Monolayers are incubated for approximately 10 days until the appearance of viral plaques.

These plaques are picked, suspended in DMEM containing 2% FCS, and used to infect a new monolayer of 293 cells. When greater than 90% of the cells show infection, viral lysates are subjected to a freeze/thaw cycle and designated as primary stocks. Recombinant virus with the correct structure is verified by preparation of viral DNA from productively-infected 293 cells, restriction analysis, and Southern blotting. Secondary stocks are subsequently generated by infecting 293 cells with primary virus stock at a multiplicity of infection of 0.01 and incubation until lysis.

The particular cell line used to propagate the recombinant adenoviruses of the present invention is not critical to the present invention. Recombinant adenovirus vectors can be propagated on, e.g., human 293 cells, or in other cell lines that are permissive for conditional replication-defective adenovirus infection, e.g., those which express adenovirus E1 gene products "in trans" so as to complement the defect in a conditional replication-defective vector. Further, the cells can be propagated either on plastic dishes or in suspension culture, in order to obtain virus stocks thereof.

When the vector is to be delivered to an animal subject, a preferred method is to percutaneously infuse an adenovirus vector construct into a native or balloon-injured blood vessel that perfuses smooth muscle cells (WO 9411506; Barr et al., Gene Therapy, 1 (1):51–58, 1994; both incorporated herein by reference) by intravenous or intra-arterial injection. Methods of delivery of foreign DNA are known in the art, such as containing the DNA in a liposome and infusing the preparation into an artery (LeClerc et al., Circulation 85:543, 1992, incorporated herein by reference), transthoracic injection (Gal et al., Lab Invest. 68:18–25, 1993, incorporated herein by reference). Other methods of delivery may include coating a balloon catheter with polymers impregnated with the foreign DNA and inflating the balloon in the region of arteriosclerosis, thus combining balloon angioplasty and gene therapy (Nabel et al., *Cardiovascular Research,* 28:445–455, 1994, incorporated herein by reference).

After delivery of an adenovirus vector construct to a smooth muscle cell, that cell is maintained under physiological conditions and for a period of time sufficient for the adenovirus vector construct to infect the cardiac cell and for cellular expression of a coding sequence contained in that construct. Physiological conditions are those necessary for viability of the smooth muscle cell and include conditions of temperature, pH, osmolality and the like. In a preferred embodiment, temperature is from about 20° C. to about 50° C., more preferably from about 30° C. to about 40° C. and, even more preferably about 37° C. pH is preferably from a value of about 6.0 to a value of about 8.0, more preferably from about a value of about 6.8 to a value of about 7.8 and, most preferably about 7.4. Osmolality is preferably from about 200 milliosmols per liter (mosm/L) to about 400 mosm/l and, more preferably from about 290 mosm/L to about 310 mosm/L. Other physiological conditions needed to sustain smooth muscle cell viability are well known in the art.

It should also be pointed out that because the adenovirus vector employed is replication defective, it is not capable of replicating in the cells that are ultimately infected. Moreover, it has been found that the genomic integration frequency of adenovirus is usually fairly low, typically on the order of about 1%. Thus, where continued treatment is required, it may be necessary to reintroduce the virus every 6 months to a year. In these circumstances, it may therefore be necessary to conduct long term therapy, where expression levels are monitored at selected intervals.

An adenovirus vector construct is typically delivered in the form of a pharmacological composition that comprises a physiologically acceptable carrier and the adenovirus vector. An effective expression-inducing amount of such a composition is delivered. As used herein, the term "effective expression-inducing amount" means that number of virus vector particles necessary to effectuate expression of a gene product encoded by a coding sequence contained in that vector. Means for determining an effective expression-inducing amount of an adenovirus vector construct are well known in the art. An effective expression-inducing amount is typically from about $10^7$ plaque forming units (pfu) to about $10^{15}$ pfu, preferably from about $10^8$ pfu to about $10^{14}$ pfu and, more preferably, from about $10^9$ to about $10^{12}$ pfu.

As is well known in the art, a specific dose level for any particular subject depends upon a variety of factors including the infectivity of the adenovirus vector, the age, body weight, general health, sex, diet, time of administration, route of administration, rate of excretion, and the severity of the particular disease undergoing therapy.

In that adenovirus is a virus that infects humans, there may be certain individuals that have developed antibodies to certain adenovirus proteins. In these circumstances, it is possible that such individuals might develop an immunological reaction to the virus. Thus, where an immunological reaction is believed to be a possibility, one may desire to first test the subject to determine the existence of antibodies.

Such a test could be performed in a variety of accepted manners, for example, through a simple skin test or through a test of the circulating blood levels of adenovirus-neutralizing antibodies. In fact, under such circumstances, one may desire to introduce a test dose of on the order of $1 \times 10^5$ to $1 \times 10^6$ or so virus particles. Then, if no untoward reaction is seen, the dose may be elevated over a period of time until the desired dosage is reached, such as through the administration of incremental dosages of approximately an order of magnitude.

In another aspect, the present invention relates to pharmaceutical compositions that may comprise an adenovirus vector gene construct dispersed in a physiologically acceptable solution or buffer. A composition of the present invention is typically administered parenterally in dosage unit formulations containing standard, well known, nontoxic, physiologically acceptable carriers, adjuvants, and vehicles as desired. The term parenteral as used herein includes intravenous, intramuscular, intraarterial injection, or infusion techniques.

Injectable preparations, for example, sterile injectable aqueous or oleaginous suspensions are formulated according to the known art using suitable dispersing or wetting agents and suspending agents. The sterile injectable preparation can also be a sterile injectable solution or suspension in a nontoxic parenterally acceptable diluent or solvent, for example, as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil can be employed including synthetic mono- or di-glycerides. In addition, fatty acids such as oleic acid find use in the preparation of injectables.

Preferred carriers include neutral saline solutions buffered with phosphate, lactate, Tris, and the like. Of course, one purifies the vector sufficiently to render it essentially free of undesirable contaminant, such as defective interfering adenovirus particles or endotoxins and other pyrogens such that it will not cause any untoward reactions in the individual receiving the vector construct. A preferred means of purifying the vector involves the use of buoyant density gradients, such as cesium chloride gradient centrifugation.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention. The following techniques and materials were used in the practice of the examples unless otherwise indicated.

Isolation of Murine SM22α cDNA Clones

The coding region of the murine SM22α cDNA was isolated by performing low stringency PCR™ using murine uterine RNA and synthetic 5' and 3' oligonucleotide PCR™ primers constructed from the previously published sequence of the rat SM22α cDNA (Nishida et al., Gene, 130:297–302, 1993). The 5' PCR™ primer was constructed to be identical to the first 34-bp of the rat SM22α cDNA with the addition of a 5' EcoRI site (5' ATCGAATTCCGCTACTCTCCTTC-CAGCCC ACAAACGACCAAGC 3', SEQ ID NO:10). The 3' primer was constructed to include the reverse complement of bp 759 to 782 of the rat SM22α cDNA with an additional 3' HindIII restriction site (5' ATCAAGCTTGGTGG-GAGCTGCCCATGTGCAGTC 3', SEQ ID NO:11). PCR™ reaction products were subcloned into EcoRI/HindIII-digested pGEM7Z (Promega, Madison, Wis.) as described elsewhere (Parmacek and Leiden, J. Biol. Chem.:264: 13217–13225, 1989). The nucleotide sequence of the murine SM22α cDNA was confirmed by sequencing of the full-length murine SM22α genomic clone. MacVector DNA sequencing software (Kodak/IBI, Rochester, N.Y.) was used for DNA sequence analyses.

To isolate the 3' untranslated region of the SM22α cDNA, $5 \times 10^5$ recombinant clones from an oligo-(dT) primed λgt11 C2C12 myotube cDNA library were screened with the [$^{32}$P]-labeled murine SM22α cDNA probe (bp 29-811) as described previously (Parmacek et al., Mol. Cell. Biol., 12:1967–1976, 1992). Twelve clones were purified to homogeneity and analyzed by Southern blot analyses as described (Parmacek et al., 1992). Two independent clones, each of which contained a poly(A) tail, were subcloned into EcoRI-digested pGEM7Z and their nucleotide sequences determined. The nucleotide sequence of the 5'-untranslated region was determined from the sequence of the SM22α genomic clone. The 5'-untranslated region was localized on the genomic clone by Southern blot hybridizations, in addition to RNase protection and primer extension analyses as described below.

Isolation of Murine SM22α Genomic Clones

Approximately $1 \times 10^6$ recombinant phage from a murine 129SV Lambda FIX II genomic library (Stratagene, La Jolla, Calif.) were screened with the 783-bp murine SM22α cDNA probe (bp 29-811) labeled with [α-$^{32}$P]dCTP, and three positive clones were purified to homogeneity as described previously (Parmacek et al., 1992). One clone (SM22-13a) was found to include the entire coding region of the SM22α gene and 9-kb of 5' flanking sequence and was used for aM subsequent subcloning and sequencing studies.

Southern Blot Analyses

High molecular weight DNA was prepared from the tails of strain 129SV mice as described previously (Parmacek et al, 1989). Southern blotting and hybridization to the radio-labeled 783-bp murine SM22α cDNA probe were performed as described previously (Parmacek et al., 1989).). Low stringency washing conditions were 2×SSC, 0.1% SDS at 50° C. High stringency washing conditions were 0.1×SSC, 0.1% SDS at 68° C.

Northern Blot Analyses

Tissues were isolated from 12-week old 129SV mice (Jackson Laboratories) as described previously (Parmacek et al., 1989). Animals were housed and cared for according to NIH guidelines in the University of Chicago Laboratory Animal Medicine Veterinary Facility. RNA was prepared from organ samples and from cultures of primary rat aortic SMCs, the rat SMC line A7r5, and non-smooth muscle cell lines including murine NIH 3T3 cells, murine C3H10T1/2 cells, monkey COS-7 cells, murine C2C12 myoblasts and myotubes, human HepG2 cells, and murine EL-4 cells by the single step guanidinium isothiocyanate protocol (Chomczynski, Biotechniques, 15:532–537, 1993). Northern blotting was performed using 10 mg of RNA per sample as described previously with the exception that 36 mg/ml of ethidium bromide was added to the RNA resuspension buffer in order to permit quantitation of the 28S and 18S ribosomal RNA subunits in each lane. Probes included the 783-bp (bp 29-811) murine SM22α cDNA and the 754-bp (bp 659-1404) murine calponin cDNA probe. Quantitative image analyses were performed using a Molecular Dynamics PhosphorImager (Sunnyvale, Calif.). Primer Extension, 5' RACE, and RNase Protection Analyses A 25-mer oligonucleotide probe constructed to include the reverse complement of base pairs +80 to +104 of the SM22α gene (5' TGCCGTAGGATGGACCCTTGTTGGC 3', SEQ ID NO:12) was 5' end labeled with [γ-$^{32}$P]ATP and T4 polynucleotide kinase. 40 mg of mouse uterine RNA was hybridized to 2×10 DPM of labeled probe and primer extension reactions performed at 42° C., 50° C. and 56° C. as described previously (Parmacek et al., 1992). 5' RACE was performed using murine uterine RNA and a synthetic antisense cDNA probe corresponding to bp 234 to 258 of the murine SM22α cDNA according to the manufacturer's instructions (Perkin Elmer, Norwalk, Conn.). RNase protection analyses were performed by subcloning the −441 to +41 murine SM22α genomic subfragment including a synthetic 3' HindIII linker into PstIIHindIII-digested pGEM4Z and performing in vitro transcription of the antisense strand of the genomic subfragment with T7 polymerase of the NcoI-linearized plasmid (NcoI cuts at bp −88 of the genomic clone) in order to obtain an antisense cRNA probe corresponding to bp −88 to +44. The HindIII linker shares sequence identity with the SM22α cDNA resulting in a cRNA probe with sequence identity initiated at bp +44 (not +41) of the SM22α genomic clone. The 142-bp probe was labeled with [α-$^{32}$P]UTP and RNase Protection Analyses were performed using the RPAII™ kit (Ambion, Austin, Tex.) according to the manufacturer's instructions. Antisense cRNA probe radiolabeled by incorporation of α-[$^{32}$P]-UTP is synthesized by in vitro transcription from linearized pBluescriptIIKST7-lacZ, which contains the lacZ gene upstream of the T7 RNA polymerase promoter, using the MaxiScript™ kit (Ambion, Austin, Tex.). Band intensity is quantified by PhosphorImager™, as previously for southern analyses described above.

Cell Culture

The rat cell line A7r5 which was derived from embryonic thoracic aorta was grown in Dulbecco's Modified Essential Media (GIBCO) supplemented with 10% fetal bovine serum (GIBCO) and 1% penicillin/streptomycin. The human hepatocellular carcinoma cell line Hep G2 was grown in Modified Eagle's Medium supplemented with 10% fetal bovine serum and 0.1 mM MEM non-essential amino acids (GIBCO). Murine lymphoma-derived EL4 cells were grown in Dulbecco's modified Eagle's Media supplemented with 10% horse serum (GIBCO). Murine NIH 3T3 cells, C3H10T1/2 cells, C2C12 myoblasts and myotubes were grown as described previously (Parmacek et al., *J. Biol. Chem.*, 265:15970–15976, 1990; Parmacek et al., *Mol. Cell. Biol.*, 14:1870–1885, 1994). Primary cultures of rat aortic SMCs were isolated from 12–16 week old Sprague Dawley rats (Charles River Laboratories, Wilmington, Mass.) using the method described previously (Chang et al., *Science*, 1995a). Virtually all cells isolated using this method stain positive with anti-smooth muscle actin monoclonal antiserum. In all studies, only early passage (passage 2 or 3) rat aortic SMCs were utilized. For the cell cycle analyses, SMCs from the third passage were placed in serum-free medium (50% Dulbecco's minimal essential medium (DMEM), 50% Ham's F-12, L-glutamine (292 mg/ml), insulin (5 mg/ml), transferrin (5 mg/ml), selenious acid (5 ng/ml)) for 72 hrs in order to synchronize the cells in $G_0/G_1$ as described previously (Chang et al., 1995a). Following 72 hrs of serum starvation, cells were stimulated to proliferate by incubation in medium containing 45% DMEM, 45% Ham's F-12 and 10% FBS. Mouse WEHI B-cells and mouse 70Z/3 pre-B lymphocytes were grown as described previously (Morrisey et al., *Dev. Biol.*, 177:309–322, 1996).

DNase I Footprinting

Nuclear extracts were prepared from the smooth muscle cell line, A7r5 (which express high levels of SM22α mRNA (Solway et al, 1995)) and NIH 3T3 cells as described previously (Parmacek et al., 1992). Three overlapping genomic subfragments (bp −441 to −256, bp −256 to −89, and bp −89 to +41) spanning the 482-bp SM22α promoter were analyzed. DNase I footprint analyses were performed with 100–150 mg of nuclear extracts prepared from the smooth muscle cell line, A7r5, or NIH 3T3 fibroblasts and the end-labeled sense and antisense strands of the murine SM22α promoter as described previously (Parmacek et al., 1994). Standard Maxam and Gilbert (G+A) sequencing reactions were run in parallel to identify the protected sequences.

Electrophoretic Mobility Shift Assays (EMSAs)

Nuclear extracts were prepared from low passage number primary rat aortic SMCs, A7r5 cells, NIH 3T3 cells, C3H10T1/2 cells, C2C12 myotubes, WEHI, 70Z/3 and EL4 cells as described by Dignam et al. *Nucleic Acids Res.* 11: 1475, (1983). EMSAs were performed in 0.25×TBE (1×TBE is 100 mM Tris, 100 mM boric acid and 2 mM EDTA) as described previously (Ip et al., *Mol. Cell. Biol.*, 14:7517–7526, 1994). The following complementary oligonucleotides (corresponding to each nuclear protein binding site identified by DNaseI footprint analysis or nuclear protein binding sites containing the specific mutations indicated (mutated nucleotides are underlined)) were synthesized with BamHI and BglII overhanging ends:

SME-1-5' AAGGAAGGGT TTCAGGGTCC TGCCCATAAA AGGTTTTTCC CGGCCGC 3' (SEQ ID NO:21);

μSME-1-5' AAGGAAGGGT TTCAGGGTCC TGCCCATAGA TCTTTTTTCC CGGCCGC 3' (SEQ ID NO:22);

SME-2- 5' CCGCCCTCAG CACCGCCCCG CCCCGAGGCC CGCAGCATGT CCG 3' (SEQ ID NO:23);

μSME-2- 5' CCGCCCTCAG CACCGCGGAT CCCCGACCCC CGCAGCATCT CCG 3' (SEQ ID NO:24);

SME-3- 5' CTCCAAAGCA TGCAGAGAAT GTCTCCGGCT GCCCCCG 3' (SEQ ID NO:25);

μSME- 3-5'CTCGGATCCA TGCTAGCAAT GAATTCGGCT GCCCCCG 3' (SEQ ID NO:26);

SME- 4- 5' TCCAACTTGG TGTCTTTCCC CAAATATGGA GCCTGTGTGG AGTG 3' (SEQ ID NO:27);

μSME- 4-5' TCCAACTTGG TGTCTT-FCCC CAAGGATCCA GCCTGTGTGG AGTG 3' (SEQ ID NO:28);

μSRF/SME-4- 5' TCCAACTTGG TGTCTTTCCC CGGATATGGA GCCTGTGTGG AGTG 3'(SEQ ID NO:29);

μYY1/SME-4- 5' TCCAACTTGG TGTCTTTCCC CAAATTAGGA GCCTGTGTGG AGTG 3'(SEQ ID NO:30);

SME-5- 5' GGGCAGGGAG GGGCGCCAGC G 3' (SEQ ID NO:31);

μSME-5- 5' GGGCAGGTAC CGAATTCAGC G 3' (SEQ ID NO:32);

SME-6- 5' GGACGGCAGA GGGGTGACAT CACTGCCTAG GCGGCCG 3' (SEQ ID NO:33);

μCREB/SME-6- 5' GGACGGCAGA GGGGATCCAT GCCTGCCTAG GCGGCCG 3' (SEQ ID NO:34);

μYY1/SME-6- 5' GGACGGCAGA GGGGATCCAT CACTGCCTAG GCGGCCG 3' (SEQ ID NO:35);

Sp1-5' CTGGCTAAAG GGGCGGGGCT TGGCCAGCC 3' (SEQ ID NO:36);

CREB/TCRα-5' CTCCCATTTC CATGACGTCA TGGTTA 3' (SEQ ID NO:37).

For cold competition studies, 5 to 100 ng of unlabeled competitor oligonucleotide was included in the binding reaction mixture. For antibody supershift studies, 1 μl of either rabbit preimmune, affinity purified rabbit or mouse IgG (Santa Cruz), α-SRF rabbit polyclonal antiserum (Santa Cruz, sc-335X), α-Sp1 rabbit polyclonal IgG (Santa Cruz, sc-059X), α-YY1 rabbit polyclonal IgG (Santa Cruz, sc-281X), α-CREB-1 mouse monoclonal IgG$_2$ (Santa Cruz, sc-271), α-ATF-1 mouse monoclonal IgA (Santa Cruz, sc-243), α-AP2 rabbit polyclonal IgG (Santa Cruz, sc-184X), or α-GATA-4 rabbit polyclonal IgG (Ip et al, 1994) was incubated with the indicated nuclear extract at 4° C. for 20 minutes prior to the binding reaction as described previously (Ip et al., 1994).

Plasmids

To assess the function of each of the six nuclear protein binding sites identified within the SM22α promoter, a series of SM22α mutant promoter-luciferase reporter plasmids were generated by PCR™-mediated site directed mutagenesis as described previously (Morrisey et al., 1996). The rous sarcoma virus (RSV) LTR-driven luciferase reporter plasmid, pRSVL, and the pMSVβgal reference plasmid have been described previously (Parmacek et al, 1992). The promoterless pGL2-Basic plasmid (Promega, Madison, Wis.) served as the cloning backbone for all of the luciferase reporter plasmids described herein. The p-5000/I1SM22luc plasmid, contains 5-kb of SM22α 5' flanking sequence, the untranslated SM22α first exon, the SM22α first intron and the first 12-bp of exon 2 of the SM22α gene subcloned 5' of the luciferase reporter gene. It was constructed by first subcloning the 8.5 kb BamHI/HindIII SM22α genomic subfragment (containing 5-kb of 5' flanking sequence, exon 1 and 3.5-kb of intron 1) into BglII/HindIII digested pGL2-Basic vector. Next, a 488-bp PCR™-generated HindIII-linkered SM2α; genomic subfragment, including at its 5' end the SM22α intron 1 HindIII restriction site, and running to bp+76 of the SM22 cDNA (which includes 12-bp of exon 2) was subcloned into the HindIII-digested vector and its correct orientation (5' to 3' relative to the luciferase reporter gene) confirmed by DNA sequence analysis. The p-5000SM22luc plasmid, containing 5-kb of SM22α 5' flanking sequence subcloned 5' of the luciferase reporter gene, was constructed by first subcloning the 2.2-kb BamHI/EcoRI SM22α genomic subfragment (corresponding to bp −5000 to −2800) into BamHI/EcoRI-digested pBluescript IIKS (Stratagene La Jolla, Calif.). Next, the 1250-bp EcoRI/NcoI SM22α genomic subfragment corresponding to bp −1338 to −89 and the 130-bp PCR™-generated genomic subfragment containing bp −88 (including the NcoI site at its 5' end) to +41 (including a HindIII linker at its 3' end) was ligated into the EcoRI/HindIII-digested vector. Then, the 1.4-kb EcoRI SM22α genomic subfragment (corresponding to bp −2800 to −1339) was subcloned into the EcoRI-digested plasmid and its orientation confirmed by DNA sequence analysis. Finally, the resulting SM22α genomic subfragment corresponding to bp −5 kb to +41 was excised from the Bluescript phagemid with BamHI and HindIII and subcloned into BglII/HindIII-digested pGL2-Basic. The p-1338SM22lucplasmid containing the 1379-bp SM22α genomic subfragment(bp −1338 to +41) subcloned 5' of the luciferase reporter in the pGL2-Basic vector, was constructed using the 1250-bp EcoRI/NcoI SM22α genomic subfragment(bp −1338 to −89) and the 130-bp (bp −88 to +41) PCR™-generated genomic subfragments described herein. The p-441 SM22luc plasmid contains the 482-bp (bp −441 to +41) PstI/HindIII SM22α genomic subfragment subcloned into BglII/HindIII-digested pGL2-Basic plasmid. The p-300SM22luc and p-162SM22luc luciferase reporter plasmids, respectively, contain the PCR™-generated bp −300 to +41, and −162 to +41 SM22α genomic subfragments (including synthetic XhoI (5' end) and HindIII (3' end) linkers), subcloned into XhoI/HindIII-digested pGL2-Basic vector. All PCR™-generated genomic subfragments were confirmed by dideoxy DNA sequence analysis.

The following SM22α mutant promoter-luciferase reporter plasmids were generated and named according to the specific nuclear protein binding site (or sites) within the promoter that was mutated (mutated nucleotides within each nuclear protein binding site are underlined):

p441SM22μSME-1 5' AAGGAAGGGT TTCAGGGTCC TGCCCATAGA TCTTTTTTCC CGGCCGC 3' (SEQ ID NO:38);

p441SM22μSME-2 5' CCGCCCTCAG CACCGCGGAT CCCCGACCCC CGCAGCATCT CCG 3' (SEQ ID NO:39);

p-441SM22μSME-3 5' CTCGGATCCA TGCTAGCAAT GAATTCGGCT GCCCCG 3' (SEQ ID NO:40);

p-441SM22μSMF-4 5' TCCAACTTGG TGTCTTTCCC CAAGGATCCA GCCTGTGTGG AGTG 3' (SEQ ID NO:41);

p441SM22μSRF/SME-4 5' TCCAACTTGG TGTCTTTCCC CGGATATGGA GCCTGTGTGG AGTG 3' (SEQ ID NO:42);

p-441SM22μYY1/SME-4 5' TCCAACTTGG TGTCTTTCCC CAAATTAGGA GCCTGTGTGG AGTG 3' (SEQ ID NO:43);

p-441SM22μSME-5 5' GGGCAGGTAC CGAATTCAGC G 3' (SEQ ID NO:44);

p-441SM22μCREB/SME-6 5' GGACGGCAGA GGGGATCCAT GCCTGCCTAG GCGGCCG 3' (SEQ ID NO:45);

p-441SM22μYY1/SME-6 5' GGACGGCAGA GGGGATCCAT CACTGCCTAG GCGGCCG 3' (SEQ ID NO:46).

In addition, several SM22α promoter-luciferase reporter plasmids were subcloned that contain mutations in two cis-acting sequences in the SM22α promoter sequence. p-441SM22μCArG contains the mutations described above in the SME-1 and SME-4 sites, and p-441 SM22μSME2/5 contains the mutations described above in the SME-2 and SME-5 sites. Each PCR™-generated SM22α promoter mutant was confirmed by DNA sequence analyses as described previously (Parmacek et al., 1992).

To identify functionally important cis-acting elements that control the expression of the SM22α gene in vivo, four transgenic vectors were cloned each of which encodes the bacterial lacZ reporter gene under the transcriptional control of the native or mutated SM22α promoter fragments. The p-5000SM22-lacZ, p-441SM22-lacZ, the p-441SM22μCArG-lacZ, and p-280SM22-lacZ plasmids, contain the 5-kb SM22α promoter, the 441-bp SM22α promoter, the 441-bp SM22α promoter with mutations in SME-1 and SME-4 (that abolish binding of SRF), and the 280-bp SM22α promoter, respectively, subcloned immediately 5' of the bacterial lacZ reporter gene in a modified pBluescript IIKS (Stratagene) plasmid.

Transfections and Luciferase Assays $1 \times 10^6$ passage three primary rat aortic SMCs, C2C12 myotubes and A7r5 cells, respectively, were split and plated 24 hours prior to transfection and transfected with either 50 or 100 μg of Lipofectin reagent (Life Technologies, Gaithersburg, Md.), 15 μg of luciferase reporter plasmid and 5 μg of the pMSVβgal reference plasmid as described previously (Parnacek et al., 1992; Ip et al., 1994; Solway et al., 1995. $1 \times 10^6$ NIH 3T3 or COS-7 were transfected with 20 μg of Lipofectin reagent, 15 μg of the luciferase reporter plasmid and 5 μg of the pMSVβgal reference plasmid as described previously (Ip et al., 1994; Forrester et al., *J. Am. Coll. Cardiol.*, 17:758–769, 1991). $1 \times 10^6$ Hep G2 cells were transfected using 360 μg of Lipofectamine reagent (Life Technologies, Gaithersburg, Md.), 26 μg of luciferase reporter plasmid and 9 μg of the pMSVβgal reference plasmid. Following transfection, cell lysates were prepared, normalized for protein content and luciferase and β-galactosidase assays were performed as described previously (Parmacek et al., 1992). All studies were repeated at least three times to assure reproducibility and permit the calculation of standard errors. Luciferase activities (light units) were corrected for variations in transfection efficiencies as determined by assaying cell extracts for β-galactosidase activities. Data are expressed as normalized light units±S.E.M.

Transgenic Mice

Transgenic mice were produced harboring the p-5000SM22-lacZ, p-441SM22-lacZ, p-441SM22μCArG-lacZ and p-280SM22-lacZ transgenes according to standard techniques as described previously (Metzger et al., Proc. Natl. Acad. USA, 90:9036, 1993). To identify transgenic founder mice, Southern blot analysis was performed using the radiolabeled lacZ probe and high molecular weight DNA prepared from tail biopsies of each potential founder. The number of copies per cell were quantitated by comparing the hybridization signal intensity (DPM) to standards corresponding to 1, 10 and 100 copies/cell using a Molecular Dynamics PhosphorImager™. At least four independent founder lines containing each transgene were identified as described previously (Parmacek and Leiden, 1989). Transgenic embryos (less than ED 15.5) and tissue sections from adult mice were fixed, stained for β-galactosidase activity and counter-stained with hematoxylin and eosin as described previously (Lin et al., *Circulation*, 82:2217–2221, 1990), except that 0.02% NP-40 was added to PBS during the fixation of whole mount embryos. In addition, to visualize the arterial system of mouse embryos, following staining for β-galactosidase activity, embryos were dehydrated in methanol for 24 h and cleared in 2:1 (V/V) benzyl benzoate:benzyl alcohol for 2 h.

Example 1

Isolation and Structural Characterization of the Murine SM22α cDNA

Murine SM22α cDNA clones were isolated using the polymerase chain reaction in conjunction with synthetic oligonucleotide primers derived from the previously published sequence of the rat SM22α cDNA (Nishida et al., 1993). The nucleotide sequence of the full-length murine SM22α cDNA is designated herein as SEQ ID NO:8. The murine SM22α cDNA encodes a 201-amino acid polypeptide, SEQ ID NO:9, with a predicted molecular mass of 22.5 kDa. It is composed of a 76-bp 5' untranslated region, a 603-bp open reading frame, and a 403-bp 3' untranslated region. Twenty three base pairs 5' of the poly(A) tail there is an A/T rich sequence (AATATA) which may function as the polyadenylation signal.

A comparison of the coding sequences of the murine and human SM22α cDNAs (Shanahan et al., 1993) demonstrated that the two sequences are 91% and 97% identical at the nucleotide and amino acid levels, respectively. In addition, a comparison of the coding sequences of the murine SM22α cDNA and the murine smooth muscle thin filament regulatory protein, calponin (Strasser et al., *Genbank* Direct Submission Accession Number Z19542, 1992), demonstrated that these two sequences are 23% identical and 32% conserved at the amino acid level. Interestingly, the protein sequence encoded by the murine SM22α cDNA exhibits partial sequence identity with the sequence of the *Drosophila* muscle protein mp20 (Lees-Miller et al., *J. Biol. Chem.*, 262:2988–2993, 1987) across the entire cDNA, suggesting that these two proteins may have evolved from a common ancestral gene. Two domains were particularly well conserved between these proteins. One domain with 14/19 amino acid identity (corresponding to amino acids 104–122 of the murine SM22α protein) may represent a calcium binding domain oriented in an EF hand conformation (Kretsinger, CRC *Crit. Rev. Biochem.*, 8:119–174, 1980). The second C-terminal conserved domain with 13/24 amino acid identity (corresponding to amino acids 158–181 of the murine SM22α protein) is a domain of unknown function. SM22α Is Encoded by a Single Copy Gene The finding of a putative calcium binding domain oriented in an EF hand conformation suggested that SM22α might be related to other members of the troponin C supergene family of intracellular calcium binding proteins including slow/cardiac troponin C, fast skeletal troponin C, calmodulin, myosin light chain and parvalbumin (Kretsinger, 1980). In order to determine whether SM22α is encoded by a single copy gene in the murine genome and whether SM22α is related to other troponin C supergene family members, the murine SM22α cDNA was used to probe Southern blots containing murine genomic DNA under both high and low stringency conditions. Under high stringency conditions, the murine SM22α cDNA probe hybridized to one or two BamHI, EcoRI, HindIII, PstI and XbaI bands, suggesting that SM22α is a single copy gene in the murine genome. Interestingly, no additional bands were demonstrated under low stringency conditions, suggesting that although the SM22α gene may have one EF hand calcium binding domain, it is not closely related to other members of troponin C supergene family.

Example 2

Expression of the SM22α (Gene

Previous studies have suggested that SM22α protein is expressed solely in smooth muscle-containing tissues of the adult and may be one of the earliest markers of the smooth muscle cell lineage (Gimona et al., *Eur. J. Biochem.,* 205: 1067–1075, 1992; Duband et al., *Differentiation,* 55 (1): 1–11, 1993; Nishida et al., 1993). To determine the in vivo pattern of SM22α gene expression, the SM22α cDNA was hybridized to Northern blots containing RNAs prepared from 12-week old murine tissues. The murine SM22α cDNA probe hybridized to one predominant mRNA species of approximately 1.2-kb. SM22α mRNA is expressed at high levels in the smooth muscle-containing tissues of aorta, small intestine, lung, spleen and uterus. In addition, prolonged autoradiographic exposures revealed very low, but detectable, levels of SM22α mRNA in heart, kidney, skeletal muscle and thymus.

In order to determine the cell-specificity of SM22α gene expression, the SM22α cDNA probe was hybridized to northern blots containing RNAs prepared from rat aortic vascular SMCs, the rat SMC line A7r5, murine NIH 3T3 and C3H10T/2 fibroblasts, the SV40-transformed monkey kidney cell line COS-7, murine C2C12 myoblasts and myotubes, the human hepatocellular carcinoma cell line Hep G2 and the murine lymphoid cell line EL4. High levels of SM22α mRNA were detected in primary rat aortic vascular SMCs and the smooth muscle cell line A7r5. Detection of a second 1.5 kb species of mRNA represents cross hybridization of the SM22α probe to the murine calponin mRNA. In addition, SM22α mRNA was expressed in both undifferentiated C2C12 myoblasts and terminally-differentiated C2C12 myotubes. Finally, a faint hybridization signal was detectable in NIH 3T3, C3H10T1/2, and Hep G2 cells after a 3-day autoradiographic exposure. Quantitative PhosphorImager™ analysis of these low level hybridization signals revealed that SM22α mRNA is expressed in these three non-myogenic cell lines at less than 1.5% the intensity of SM22α gene expression in A7r5 and primary SMCs. Thus, in addition to primary SMCs and SMC lines, SM22α mRNA is expressed in other embryonic skeletal muscle cell lineages such as C2C12 myoblasts and myotubes, but not in other non-myogenic cell lineages.

SM22α Is Expressed in Both Cell Cycle Arrested and Proliferating SMCs

Within the tunica media of the arterial wall the vast majority of vascular SMCs are maintained in a non-proliferating, quiescent state and express contractile proteins (Owens et al., 1986; Rovner et al., 1986; Taubman et al., 1987; Ueki et al., 1987; Gimona et al., 1990; Shanahan et al;, 1993; Ross, Nature, 362:801, 1993; Forrester et al., 1991). However, in response to vascular injury, SMCs migrate from the tunica media to the intimal layer, proliferate and assume a "synthetic phenotype" (Ross, 1986; Schwartz et al., 1986; Zanellato et al., 1990; Ross, 1993; Forrester et al., 1991; Schwartz et al., 1992; Liu et al., 1989). Previous studies have demonstrated that many genes encoding vascular SMC contractile proteins are down-regulated during this process (Owens et al., 1986; Rovner et al., 1986; Ueki et al., 1987; Gabbiani et al., Proc. Natl. Acad. Sci. USA 78:298, 1981). Thus, the SM22α gene may be unique in that its expression is not differentially regulated during progression through the cell cycle. In order to address this question, cultures of low passage number primary rat aortic SMCs were synchronized in the $G_0/G_1$ stage of the cell cycle by serum starvation for 72 hrs. FACS analyses revealed that under these conditions approximately 90% of cells are arrested in $G_0/G_1$ (Chang et al., 1995a). The cells were then serum-stimulated and RNA was prepared from replicate cultures at the time of serum stimulation ($t_0$), and at 8 hrs, 12 hrs, 16 hrs, and 24 hrs post-stimulation. After serum stimulation, the arrested vascular SMCs begin to pass through the $G_1/S$ checkpoint of the cell cycle at approximately 12 hrs and by 24 hrs post-stimulation greater than 50% of cells are in the S and $G_2/M$ phases of the cell cycle (Chang et al., 1995a). A northern blot analysis demonstrated no differences in SM22α gene expression in cell cycle arrested versus proliferating SMCs as assessed by quantitative PhosphoroImager™ analysis of the hybridization signal. Thus, in contrast to other smooth muscle contractile proteins, such as smooth muscle myosin heavy chain (Rovner et al., 1986), smooth muscle α-actin (Owens et al., 1986) and calponin, SM22α appears to be constitutively expressed at high levels in both quiescent and proliferating vascular SMCs.

Example 3

Isolation and Structural Characterization of a SM22α Genomic Clone

A full length murine SM22α genomic clone of 20-kb was isolated by screening a murine 129SV genomic library with a SM22α cDNA probe under high stringency conditions. Exons were identified by hybridization with specific cDNA fragments and their boundaries confirmed by DNA sequence analysis. The nucleic acid sequence of the genomic clone is designated herein as SEQ ID NO:1, containing exon 1, SEQ ID NO:2, containing exons 2, 3 and 4, and SEQ ID NO:6, containing exon 5. There is approximately a 4 kb gap between SEQ ID NO:1 and SEQ ID NO:2, and approximately a 450 base gap between SEQ ID NO:2 and SEQ ID NO:6. The amino acid sequences are encoded by exons 2, 3 and 4 and are designated herein as SEQ ID NO:3, SEQ ID NO:4, SEQ ID NO:5 and SEQ ID NO:7. The murine SM22α gene is composed of five exons spanning 6.2-kb of genomic DNA.

The transcriptional start site of the SM22α gene was identified by RNase protection, primer extension and 5' RACE PCR™ analyses. Primer extension analyses utilizing an antisense synthetic oligonucleotide corresponding to bp 80-104 of the SM22α cDNA resulted in a major extended product of 104-bp (arrow) which was generated at reaction temperatures up to 56° C. In addition, 5' RACE PCR™ was performed utilizing an antisense oligonucleotide primer corresponding to bp 234-258 of the SM22α cDNA. DNA sequence analyses of eight random 5' RACE clones revealed a transcriptional start site 76-bp 5' of the initiation codon in seven of eight clones and 72-bp 5' of the initiation codon in one of eight clones. RNase protection analyses were also performed using an antisense cDNA probe corresponding to bp −88 +44 of the SM22α genomic sequence as deduced by DNA sequence and Southern blot analyses. These analyses revealed a major protected fragment of 44-bp (arrow) corresponding to a transcriptional start site 76-bp 5' of the initiation codon. In addition, a second, minor (20% relative signal intensity) protected fragment of 54-bp was also demonstrated. Taken together, these data allowed the identification of the major transcriptional start site of the murine SM22α gene 76-bp 5' of the initiation codon.

The complete coding sequence and 1339-bp of 5' flanking sequence of the SM22α gene was determined and each of the splice junctions conforms to the consensus splice donor-acceptor patterns as described by Breathnach and Chambon (Breathnach et al., *Annu. Rev. Biochem*, 50, 349–383, 1981). In order to identify potential transcriptional regulatory elements, 1339-bp of 5' sequence flanking the cap site was searched for a variety of transcriptional regulatory elements using MacVector DNA sequencing software (Kodak/IBI). The nucleotide sequence TTTAAA, which might function as a TATA box was present 29-bp 5' of the start site. A consensus CAAT box was not identified in the immediate 5' flanking region of the SM22α gene. A computer homology search for previously described muscle-specific and/or skeletal or cardiac muscle lineage-restricted transcriptional regulatory elements revealed five consensus E boxes/bHLH myogenic transcription factor binding sites (CANNTG [Olson, *Genes Dev.*, 4, 1454–1461, 1990; Tapscott et al., *J. Clin. Invest.*, 87:1133–1138, 1991; Lassar et al., *Cell*, 58 (5): 823–311, 1989]) located at bps −534, −577, −865, −898, −910, and −1267, three consensus GATA-4 binding sites (WGATAR [Evans et al., *Proc. Natl. Acad. Sci.* (*USA*), 85:5976–5980, 1988]) located at bps −504, −828, −976, and two AT-rich, potential MEF-2/rSRF binding sites (YTAWAAATAR, SEQ ID NO:13 [Gossett et al., *Mol. Cell. Biol.*, 9:5022–5033, 1989]) located at bps −407 (TT-tAAAATcG, SEQ ID NO:14, small letters denote mismatches from the consensus MEF-2 sequence) and −770 (TTcAAAATAG, SEQ ID NO:15). In addition, functionally important nuclear protein binding sites which have been identified in previously characterized skeletal and cardiac-specific transcriptional regulatory elements included two consensus CArG/SRF binding sites (Minty et al., *Mol. Cell. Biol.* 6:2125, 1986) located at bps −150 and −273 and one CACC box (Dierks et al., *Cell*, 32:695–706, 1983) located at bp −104. Finally, four AP2 (CCCMNSSS, SEQ ID NO:16 [Mitchell et al., *Cell*, 50:847–851, 1987]), one Sp1 (KRG-GCKRRK, SEQ ID NO:17 [Dynan et al., *Cell*, 35:79–87, 1983]), and two NF-IL6 (TKNNGNAAK, SEQ ID NO:18 [Akira et al., *EMBO J*, 9 (6):1897–906, *Cell*, 35:79–87, 1990]) binding sites were located in the 5' flanking region.

Example 4

Identification of the cis-Acting Transcriptional Regulatory Elements that Control SM22α Gene Expression In order to identify the functionally important cis-acting sequences that regulate transcription of the SM22α gene in SMCs, a series of transient transfections were performed using SM22α-luciferase reporter constructs and primary rat aortic vascular SMCs and the SMC line, A7r5, both of which express high levels of SM22α mRNA. Transfection of A7r5 cells with the plasmid p-5000/I1SM22luc, containing 5-kb of 5' flanking sequence and the entire 4-kb SM22α intron 1 sequence (the initiation codon is located in exon 2), resulted in a 250–300-fold induction in luciferase activity as compared to the promoterless control plasmid, pGL2-Basic. This level of transcriptional activity was comparable to that obtained following transfection of A7r5 cells with the RSV-containing luciferase reporter plasmid, pRSVL. In order to determine whether this transcriptional activity was due to the immediate 5' flanking region of the SM22α gene, or alternatively, was due to a transcriptional regulatory element located within the first intron of the SM22α gene, the activities of the p-5000/I1SM22luc and p-5000SM22luc plasmid were compared. Transfection of A7r5 cells with the p-5000SM22luc plasmid, containing only 5-kb of 5' flanking sequence, resulted in high-level transcription of the luciferase reporter gene comparable (on a molar basis) to levels obtained with the p-5000/I1SM22luc plasmid. Thus, the 5' flanking region of the SM22α gene contains cis-acting sequence elements required for high-level transcription in A7r5 cells.

To further localize the 5' flanking elements of the SM22α gene that direct high-level expression in SMCs, a series of 5' deletion mutants were transfected into both A7r5 cells and primary cultured rat aortic vascular smooth muscle cells. In both A7r5 cells and primary vascular SMCs, the p-441SM22luc plasmid, containing 441-bp of 5' flanking sequence, increased transcription of the luciferase reporter to levels comparable to the p-5000SM22luc plasmid and the p-1338SM22luc plasmids. However, transfection of both A7r5 cells and primary vascular SMCs with the luciferase reporter plasmids p-300SM22luc and p-162SM22luc containing 300-bp and 162-bp, respectively, of 5' flanking sequence resulted in 50% and 90% reductions in normalized luciferase activities as compared with those obtained with the p-441SM22luc. These data demonstrated that 441-bp of SM22α 5' flanking sequence, containing the endogenous SM22α promoter, is sufficient to direct high-level transcriptional activity in both A7r5 cells and primary rat aortic SMCs.

Example 5

Cellular-Specificity of the SM22α Promoter

In order to characterize the cellular-specificity of the SM22α promoter sequence, the transcriptional activities of the 441-bp SM22α promoter containing plasmid, p441SM22luc, was compared to the positive control plasmid containing the rous sarcoma virus LTR, pRSVL, in primary rat vascular SMCs, the smooth muscle cell line A7r5, NIH 3T3 fibroblasts, COS-7, and Hep G2 cells. Consistent with the lineage-restricted pattern of SM22α mRNA expression demonstrated in these cell lines, the promoter-containing plasmid, p-441 SM22luc, was active in primary rat aortic SMCs and A7r5 cells, increasing transcription of the luciferase reporter gene approximately 2500-fold and 540-fold, respectively, over that induced by transfection with the promoterless pGL2-Basic plasmid (FIG. 1). This level of promoter activity was comparable to levels obtained following transfection of these cells with the RSV LTR-driven positive control plasmid (FIG. 1). In contrast, the 441-bp SM22α promoter was inactive in NIH 3T3, COS-7 and Hep G2 cells (FIG. 1).

DNA sequence analyses revealed that this 441-bp promoter contains two CArG/SRF boxes (Minty et al., 1986), a CACC box (Dierks et al., 1983), and one A/F-rich, potential MEF-2/rSRF binding site (Gossett et al., 1989), cis-acting elements which have each been demonstrated to be involved in the transcriptional programs that regulate skeletal and cardiac muscle-specific gene expression. However, unlike most previously described skeletal muscle-specific transcriptional regulatory elements, this sequence lacked a canonical E box binding site for the myogenic bHLH transcription factors (Tapscott et al., 1991; Lassar et al., 1989). Thus, the endogenous 441-bp SM22α promoter contains all of the cis-acting sequence elements required to recapitulate the smooth muscle lineage-restricted pattern of SM22α gene expression demonstrated in vivo.

Example 6

Generation of SM22α-βgal Transgenic Mice

A reporter construct was first prepared in which the 441-bp minimal SM22α promoter was subcloned immediately 5' of the bacterial β-galactosidase reporter gene (lacZ). The transgenic vector was generated from a pBluescript-KS phagemid containing AscI restriction sites flanking the polylinker sequence. This construct is referred to herein as –441SM22lacZ. The transgene was microinjected into oocytes that were transplanted into pseudo-pregnant hosts as described in Metzger et al., 1993 (incorporated herein by reference). To identify transgenic founder mice, Southern blot analysis was performed using the radiolabeled lacZ probe and high molecular weight DNA prepared from tail snips of each potential founder pup. The radiolabeled lacZ cDNA probe hybridized to the expected 4.2 kb BamHI-digested band in 4 of 17 pups analyzed. The four founders contained between 5 and 160 copies per cell as assessed by comparing the hybridization signal intensity (DPM) to standards corresponding to 1, 10 and 100 copies per cell using a Molecular Dynamics PhosphorImager™.

The F1 –441SM22lacZ #14 male was crossed with a CD-1 female and E11.5 embryos from this litter were isolated, genotyped (using PCR™), fixed and stained for β-galactosidase activity. Transgenic embryos were easily distinguished from their non-transgenic litter mates by the obvious blue staining along their distal somites. This pattern correlated with the transient pattern of SM22α gene expression observed in the developing somites. In ED11.5 embryos, the endogenous SM22α gene is expressed throughout the primitive heart tube, developing somites, dorsal aorta and the forming branch arteries (Li et al, 1996a). Whole mount staining of ED11.5 embryos demonstrated high level β-galactosidase activity throughout the developing arterial system. Blue staining was observed throughout the dorsal aorta, the carotid and vertebral arteries, the cerebral arteries, the umbilical arteries and the aortic arches. A high power section through the iliac artery, demonstrated that expression of the lacZ transgene was restricted to 1–2 layers of cells underlying the arterial endothelium. In addition, β-galactosidase activity was detected within the myotomal component of the developing somites and within the bulbo-truncus region (future outflow tract) and at low levels within the bulbo-cordis region (future right ventricle) of the primitive heart. β-galactosidase activity was not detected within the future left ventricle, left atrium or right atrium at this stage of embryonic development. Surprisingly, although the SM22α gene is expressed at high levels in smooth muscle cells lining the pulmonary airways, as well as within the gastrointestinal and genitourinary tracts, no β-galactosidase activity was detected in the developing lung buds, gastrointestinal mucosa, or the uterine or bladder mucosa during late murine embryogenesis or postnatal development. Thus, the 441 bp SM22α promoter is necessary and sufficient to activate transcription in vascular SMC's in a lineage-restricted fashion in transgenic mice. In addition, this minimal promoter element contains cis-acting sequences required to activate transcription of the SM22α gene in the developing somites. These data also demonstrate that SM22α gene expression is regulated at the level of transcription.

Furthermore, the normalized luciferase activity obtained with the 300-bp promoter was still 100-fold above that obtained with promoterless control plasmids in these transient transfection assays. To determine whether a 280-bp SM22α promoter fragment (bp –280–+41) was sufficient to direct arterial SMC-specific gene expression, the inventors produced eight independent lines of transgenic mice in which the lacZ gene was placed under the transcriptional control of the 280-bp SM22α promoter. These mice contained between 2 and 34 copies of the transgene per cell. The 280-bp of 5' flanking sequence was sufficient to direct high level β-galactosidase activity (blue staining) to arterial SMCs and the myotomal component of the somites of ED11.5 mice. Virtually identical patterns of transgene expression were demonstrated in 4 independent lines analyzed at ED11.5 in which copy numbers varied between 2 and 34 copies per cell. Interestingly, dense blue staining was detected within the cardiac outflow tract (a neural crest derivative) while a somewhat patchy pattern of blue staining was present in the developing arterial system (which is derived from lateral mesoderm and neural crest). Higher power sections confirmed that virtually every cell within the cardiac outflow tract stained blue. Interestingly, dense blue staining was detected within the mesenchymal cells that compose the aorticopulmonary spiral septum which is present at ED11.5. In addition, most, but not all, cells underlying the epithelium of the developing arteries stained blue. Taken together, these data demonstrate that the 280-bp SM22α promoter is sufficient to program lineage-restricted transcription in arterial SMCs and the developing somites. However, in contrast to the endogenous pattern of SM22α gene expression, the 441-bp (and 280-bp) SM22α promoter does not contain the cis-acting elements that control SM22α transcription in either visceral (gastrointestinal, uterine, bladder, and bronchial) or venous SMCs nor in the primitive heart tube. Finally, the inventors observed virtually the same arterial SMC-specific pattern of expression using the 5000-bp SM22α promoter in transgenic mice. These data strongly suggest that distinct transcriptional programs distinguish tissue-restricted subsets of SMCs (even within the vasculature). Xgal tissue staining The lung, heart, liver, kidney, spleen, testis or ovary, and skeletal muscle are excised from euthanized animals, and stained to reveal β-galactosidase activity. If β-galactosidase activity is evident in non-transgenic mice, the transgenic lines are generated using a nuclear localizing β-galactosidase isoform to minimize false-positive staining (Hughes and Blau. 1990). To reveal β-galactosidase activity, tissues are washed in PBS, then fixed in 1.25% glutaraldehyde (lung is fixed as below). After washing in $Ca^{+2}$- and $Mg^{+2}$-free buffer, tissues are incubated overnight in the dark in Xgal solution (50 mM Tris HCl pH 7.5, 2.5 mM potassium ferriferrocyanide, 15 mM NaCl, 1 mM $MgCl_2$, 0.5 mg/ml Xgal), then paraffin embedded; 4 micron sections are counterstained with eosin.

Data Analysis

The tissue and cellular distribution of Xgal staining, reflecting SM22α promoter transcriptional activity, is recorded for each transgenic line studied, and compared qualitatively among experimental conditions. Quantitative assessment of lung and tracheal SM22α promoter transcriptional activity is also performed by RNase protection assay for lacZ mRNA, which is compared among study groups using ANOVA followed by multiple range testing. To test whether potential differences in lacZ mRNA levels might stem from different amounts of smooth muscle among groups, airway smooth muscle area vs. circumference curves is compared between groups as described by James et al. (1989); pulmonary arterial area vs. circumference curves are likewise compared.

Example 7

Expression of SM22α in Lung

SM22α mRNA by is detected in the lungs by in situ hybridization. A digoxigenin-labeled cRNA corresponding to the reverse complement of mouse SM22α cDNA bp 644 to 1007 was prepared, by in vitro transcription (MaxiScript™ Kit, Ambion, and Genius™ 4 Kit, Boehringer Mannheim). In situ hybridization was performed on a lung specimen obtained at autopsy from a patient without lung disease. Hybridized probe is detected immunohistochemically with an anti-dioxigenin antibody linked to alkaline phosphatase. The SM22α cRNA binds selectively to airway smooth muscle and to pulmonary vascular smooth muscle; black anthracotic pigment was also evident in this specimen (typical of urban dwellers).

Example 8

Adenovirus Mediated Expression of a Heterologous Gene Product In Vitro

Figure 3A:
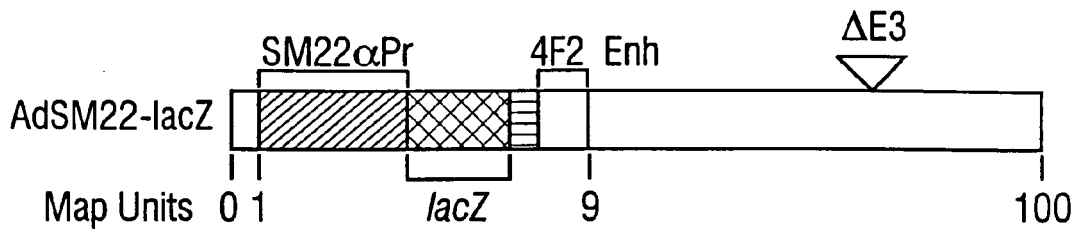
FIG. 3A. Schematic representations of the AdSM22-lacZ and AdCMV-lacZ adenoviral vectors. The AdSM22-lacZ vector (upper panel) encodes the bacterial lacZ reporter gene (black box) and bovine growth hormone polyadenylation signal (box with horizontal lines) under the transcriptional control of the 441-bp murine SM22α promoter (box with diagonal lines) and the 450-bp human 4F2 transcriptional enhancer (white box). The E1 and E3 regions of the Ad5Sub360 adenoviral genome were deleted (ΔF3) rendering the virus replication-defective. The AdCMV-lacZ control virus encodes the lacZ reporter gene (black box) under the transcriptional control of the cytomegalovirus immediate early gene promoter enhancer (box filled with dots).

The 441-bp murine SM22α promoter has been shown previously to program arterial SMC-specific gene expression in transgenic mice (Kim et al., 1997; Li et al., 1996b; Moessler et al., 1996). To test whether the SM22α promoter could be utilized to restrict the expression of a recombinant gene product encoded by a RDAd to SMCs, a RDAd (AdSM22-lacZ) was constructed containing the bacterial lacZ reporter gene under the transcriptional control of the murine SM22α promoter (FIG. 3A, upper panel). In the studies described here, the activity of AdSM22-lacZ was compared to that of the control virus, AdCMV-lacZ (Tripathy et al., *Proc. Natl. Acad. Sci. USA*, 91:11557–11561, 1994), in which the bacterial lacZ reporter gene is under the transcriptional control of the ubiquitously active cytomegalovirus (CMV) immediate early gene promoter/enhancer (FIG. 3A. lower panel).

Figure 3B:
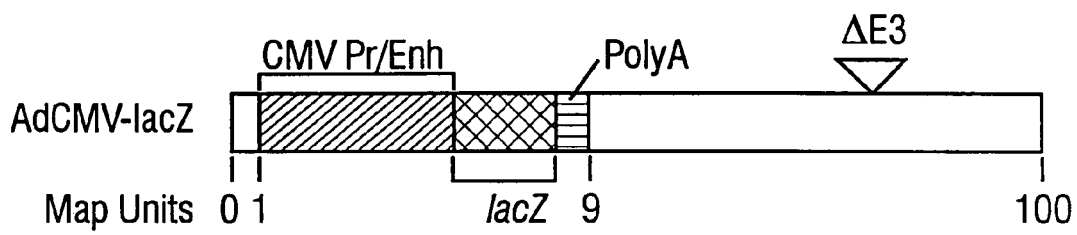
FIG. 3B. Comparison of the activity of AdSM22-lacZ and the AdCMV-lacZ control virus in primary cultures of rat aortic smooth muscle cells (VMSC) and human umbilical vein endothelial cells (HUVEC). Primary cultures of VSMCs or HUVECs were infected with 1-, 10-, and 100-PFU of either AdSM22-lacZ (black squares-HUVEC and black circles-VSMC) or AdCMV-lacZ (open squares-HUVEC and open circles-VSMC) and the % of cells expressing β-galactosidase activity was quantitated 72-h post-infection. Data are expressed as the mean percentage of cells expressing βgal activity ±S.E.M.
Figure 4:
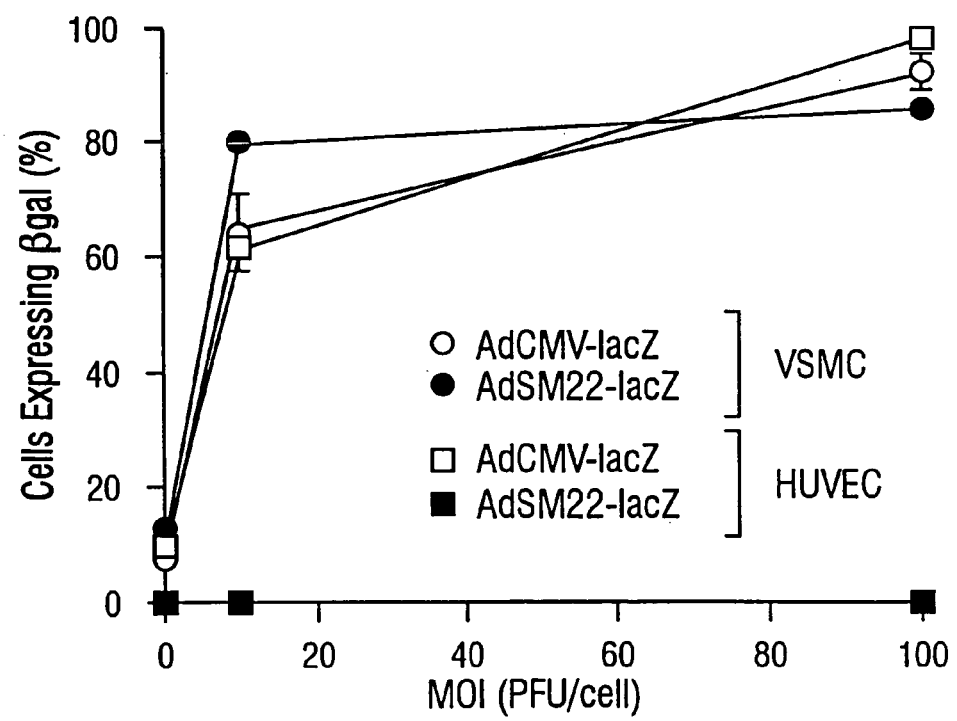
FIG. 4. Comparison of β-gal expression from CMV and SM22α promoters. Percentage of cells expressing β-gal from adenoviral vectors, where the β-gal expression is driven by either the CMV promoter (open) or the SM22α (filled), as a function of multiplicity of infection (MOI) is depicted. Circles represent experiment is vascular smooth muscle cells (VSMC) and squares represent experiment in human vascular endothelial cells (HUVEC).

To assess the activity of AdSM22-lacZ in cells transduced in vitro, replicate cultures of primary rat aortic SMCs were infected with 1-, 10- and 100-plaque forming units (PFU)/cell of either AdSM22-lacZ or AdCMV-lacZ and the fraction of cells expressing histochemically identifiable β-galactosidase activity (as assessed by blue staining with Xgal) was quantitated. As shown in FIG. 3B, 12, 80, and 88% of cells expressed the lacZ transgene following infection with 1-, 10- and 100-PFU/cell, respectively, of AdSM22-lacZ. The fraction of cells expressing β-galactosidase was comparable to that observed following infection of replicate cultures with the control AdCMV-lacZ virus (FIG. 3B). Consistent with these findings, 10, 70 and 90%, respectively, of immortalized A7r5 vascular SMCs expressed the lacZ transgene following infection with 1-, 10-and 100-PFU/cell of AdSM22-lacZ. This efficiency of transgene expression was, again, comparable to that observed following infection of this immortalized SMC line with the AdCMV-lacZ control virus.

To determine whether the SM22α promoter restricted expression of the lacZ reporter gene to SMCs, primary human umbilical vein endothelial cells (HUVECs) and NIH 3T3 fibroblasts were infected with AdSM22-lacZ or the AdCMV-lacZ control virus. In contrast to the high efficiency of transgene expression observed following AdSM22-lacZ-mediated infection of primary and immortalized SMCs (FIG. 3B), β-galactosidase activity was not detectable in HUVECs or NIH 3T3 cells following infection with AdSM22-lacZ (FIG. 3B). In contrast, 10, 60, and 93% of HUVECs expressed histochemically detectable β-galactosidase activity following infection with 1-, 10-, and 100-PFU, respectively, of the AdCMV-lacZ control virus (FIG. 3B). Similarly, approximately 50% of NIH 3T3 cells expressed-detectable β-galactosidase activity following infection with 100-PFU/cell of the AdCMV-lacZ control virus.

Southern blot analyses of DNA harvested from HUVECs infected 72-h previously with AdSM22-lacZ demonstrated the presence of the lacZ transgene in these cells. The hybridization signal was comparable in intensity to that obtained with DNA harvested from HUVECs infected with the AdCMV-lacZ control virus thereby confirming efficient infection of these cells by AdSM22-lacZ. The different sizes of the lacZ hybridizing bands seen in this study is consistent with the expected patterns of restriction endonuclease digestion of each adenoviral vector with BglII. Despite the fact that AdSM22-lacZ and AdCMV-lacZ both efficiently infected HUVECs, no lacZ transgene mRNA was detected in the AdSM22-lacZ infected HUVECs by Northern blot analysis. In contrast, HUVECs infected with the control AdCMV-lacZ virus expressed abundant lacZ mRNA. Taken together, these data demonstrated that AdSM22-lacZ programs SMC-specific transgene expression in vitro and confirmed that the lineage-restricted expression of the transgene was regulated at a transcriptional or post-transcriptional level.

The pAdSM22 plasmid was generated by subcloning the 441-bp murine SM22α promoter (Solway et al., 1995) into ClaI (5' end)/HindIII (3' end)-digested pAdEF1 (KN) plasmid (Tripathy et al., 1994). The pAdSM22-lacZ plasmid was generated by subcloning the HindIII (5' end)/BglII (3' end)-linkered bacterial lacZ reporter gene into the HindIII/BamHI-digested pAdSM22 plasmid. The AdSM22-lacZ adenovirus encoding the bacterial lacZ reporter gene under the transcriptional control of the murine SM22α promoter and the human 4F2 heavy chain transcriptional enhancer (Karpinski et al., *Mol. Cell. Biol.*, 9:2588–2597, 1989) was generated by recombination in 293 cells between the pAdSM22-lacZ plasmid DNA and E1- and E3-deleted Ad5Sub360 genomic DNA digested with XbaI and ClaI as described previously (Barr et al., 1994) The structure of this virus was confirmed by Southern blot analyses. The AdCMV-lacZ RDAd encoding the bacterial lacZ reporter gene under the transcriptional control of the cytomegalovirus (CMV) immediate early gene promoter/enhancer has been described previously (Barr et al., 1994). Recombinant viruses were plaque purified three times to avoid contamination with replication-competent virus. High titer adenoviral stocks were prepared by infecting 293 cells with 2- to 5-plaque forming units (PFU) of virus per cell as described previously (Barr et al., 1994). Titers of each cesium chloride purified viral stock were determined from the absorbance at 260 nm (1 absorbance unit=$10^{10}$ PFU/ml) and were confirmed by plaque assay as described previously (Barr et al., 1994).

The studies described in this example were performed as follows: Primary rat aortic SMCs were isolated from 12- to 16-wk old Sprague Dawley rats and grown as described previously (Chang et al., 1995a). Virtually all cells stain positive for expression of SM-α-actin when isolated using this technique (Solway et al., 1995). In all experiments only third passage primary rat aortic SMCs were utilized. Immortalized rat vascular A7r5 SMCs, passage 4 human umbilical vein endothelial cells (HUVECs), and mouse NIH 3T3 fibroblasts were grown as described previously (Kim et al., 1997). Cells were placed in medium containing 2% fetal bovine serum (FBS) and infected with either 1-, 10- or 100-PFU/cell of purified adenoviral stocks. Following infection, cells were washed in PBS and placed in growth medium containing 10% FBS. 72-h post-infection, cells were harvested for preparation of DNA and RNA, or were fixed and stained for β-galactosidase activity with X-gal as described (Lin et al., 1990). The unstained and blue-stained (β-gal$^+$) cells from 10 representative high power fields were counted in each section and the percentage of β-gal$^+$ cells calculated. The data are expressed as % β-galactosidase positive cells ±S.D. All experiments involving animals were approved by the University of Chicago Committee on Animal Care and Use. The Sprague-Dawley rats were housed and cared for according to NIH guidelines in the A. J. Carlson Animal Research Facility at the University of Chicago.

Southern and Northern blot analyses were performed as described previously (Parmacek and Leiden, 264:13217–13225, 1989). The polymerase chain reaction (PCR)-generated 485-bp bacterial lacZ probe (which corresponds to bp 962-1448 in the pCMV plasmid (Clonetech)) was radiolabelled and used for the Southern and Northern blot analyses. Quantitative image analyses were performed using a Molecular Dynamics PhosphorImager (Sunnyvale, Calif.).

Example 9

Intra-Arterial Administration of RDAd in Uninjured and Balloon-Injured Rat Carotid Arteries After induction of anesthesia and intubation, the left and right carotid arteries of adult Sprague-Dawley rats were isolated and a balloon-injury was created by dilatation with a 2F Fogarty catheter as described previously (Chang et al., 1995a). A 24-gauge intravenous catheter was introduced into the lumen of uninjured or balloon-injured arterial segments and $2 \times 10^9$-PFU of AdSM22-lacZ or AdCMV-lacZ was instilled into the isolated arterial segment for 5 minutes. Seven days following infection, rats were euthanized and the isolated segments of carotid artery were removed, fixed in 1.25% glutaraldehyde, and stained for β-galactosidase activity with X-gal as described previously (Lin et al., 1990). Photomicroscopy was performed using Kodak EPT 160 film and a Zeiss Axiophot micro scope.

To determine whether the SM22α promoter could be used to restrict adenovirus-mediated transgene expression to arterial SMCs in vivo, $2 \times 10^9$ PFU of either AdSM22-lacZ or the control AdCMV-lacZ virus were introduced into isolated segments of uninjured and balloon-injured rat carotid arteries. Diffuse blue staining of the vascular endothelium was observed seven days following administration of the control AdCMV-lacZ virus into the uninjured rat carotid artery. In addition, rare cells within the adventitia also stained blue. In contrast, when AdSM22-lacZ was introduced into the uninjured rat carotid artery, β-galactosidase activity was not observed within either endothelial or adventitial cells. However, rare lacz-expressing SMCs were observed in the superficial (abluminal) layer of the tunica media. These data suggested that the SMC-specificity of AdSM22-lacZ transgene expression is maintained following intra-arterial administration of AdSM22-lacZ into an isolated segment of the uninjured rat carotid artery.

To determine the cell-specificity of transgene expression in balloon-injured rat carotid arteries, $2 \times 10^9$-PFU of AdSM22-lacZ was instilled into an isolated segment of the rat carotid artery for 5 minutes immediately following balloon injury. Seven days post-infection, the injured arterial segments were isolated and the pattern of β-galactosidase expression was compared to that observed in the uninfected balloon-injured contra lateral artery. In contrast to the low level β-galactosidase activity observed in the uninjured carotid artery infected with the AdSM22-lacZ virus, higher efficiency gene transfer was achieved in these balloon-injured arterial segments. The majority of the SMCs expressing β-galactosidase activity were located within the tunica media. In addition, rare cells within the neointima also stained light blue. Consistent with previous reports, gene transfer was preferentially observed in the SMCs underlying the site of neointimal proliferation. Finally, lacZ transgene expression was not observed in endothelial cells at the margins of the vessel wall injury, where endothelial cells remained intact. Taken together, these data demonstrated that the AdSM22-lacZ virus maintains its SMC-specific pattern of transgene expression following intra-arterial administration and that it can be used to efficiently transduce arterial SMCs in the balloon-injured rat carotid artery.

Example 10

Intravenous Administration of RDAd

Intravenous administration of RDAd results in high level gene transfer to the liver and lung thereby potentially limiting the utility of these viruses in some clinical settings (Kashyap et al., 1995; Johns et al., 1995; Miller and Vile, 1995). 12–16 week old Sprague-Dawley rats were injected intravenously with $10^9$- or $10^{10}$-PFU of AdSM22-lacZ or AdCMV-lacZ, respectively. Liver function tests were performed on serum samples obtained 7 days following infection using Kodak DT60II and DTSCH automated analyzers. To determine the significance of alterations in liver function tests observed between control, AdSM22-lacZ-infected, and AdCMV-lacZ-infected rats, Student's t tests were performed. 7-days post-injection, rats were euthanized and the injected tissue, as well as the liver, lung, kidney, and carotid arteries were isolated, washed, fixed and stained for β-galactosidase activity with X-gal as described previously (Lin et al., 1990).

LacZ expression was observed throughout the livers of rats infected with the AdCMV-lacZ control virus. In addition, focal patches of β-gal$^+$ cells were observed within perivascular regions of the lung of AdCMV-lacZ-infected rats. In contrast, seven days after infection with AdSM22-lacZ, histological sections of both the liver and lung were indistinguishable from those obtained from uninfected control rats. These data suggest that in contrast to RDAd containing virally-driven and/or ubiquitously active transcriptional regulatory elements, AdSM22-lacZ restricts transgene expression to SMCs following intravenous administration.

To determine whether intravenous administration of AdSM22-lacZ caused abnormalities in liver function despite the finding that the lacZ reporter gene encoded by this virus was not expressed in this tissue, adult Sprague Dawley rats were injected intravenously (IV) with $-10^{10}$-PFU of the AdSM22-lacZ virus and liver function tests were performed on serum samples obtained seven-days post-infection. No statistically significant elevations in serum alkaline phosphatase (AP), alanine aminotransferase (ALT), aspartate aminotransferase (AST), γ-glutamyltranspeptidase (GGT), total bilirubin, total protein and albumin were observed in rats infected with the AdSM22-lacZ virus (see Table 1) (p>0.05). However, small, but consistent, elevations in the mean serum concentrations of ALT, AST, AP were observed. In contrast, statistically significant elevations in ALT and AST serum concentrations were observed seven days following intravenous administration of $10^{10}$-PFU of the AdCMV-lacZ control virus (p<0.05). In addition, increased serum concentrations of AP and bilirubin were observed in rats receiving $1 \times 10^{10}$-PFU of the AdCMV-lacZ virus (p<0.09). Thus, intravenous administration of high doses of AdSM22-lacZ did result in mild elevations in liver function tests. However, the liver function test abnormalities were significantly less marked than those observed in rats infected with identical doses of the AdCMV-lacZ control virus.

TABLE 1

|  | ALT | AST | AP | Bili | Alb |
|---|---|---|---|---|---|
| Control | 61 ± 4 | 97 ± 8 | 229 ± 38 | 0.1 ± 0.0 | 2.9 ± 0.1 |
| $10^{10}$SM22-lacZ | 104 ± 33 | 137 ± 21 | 306 ± 37 | 0.1 ± 0.0 | 3.7 ± 0.2 |
| $10^{10}$CMV-lacZ | 153 ± 16* | 166 ± 21* | 442 ± 103** | 0.3 ± 0.2** | 3.3 ± 0.2 |

Data are expressed as mean ± S.E.M.
*p < 0.05 versus control values
**p < 0.09 versus control values Example 11

Direct Injection of RDAd into Visceral SMCs and Skeletal Muscle

Direct injection of AdSM22-lacZ into SMC-containing tissues and skeletal muscle was performed following induction of anesthesia and intubation as described above. $10^9$-PFU of the AdSM22-lacZ virus was injected directly with a 30-gauge needle into the wall of the ureter, the bladder wall or intramuscularly. The site of each injection was marked by a suture. Seven days after injection, the sites of injection were isolated, fixed and stained for β-galactosidase activity as described (Lin et al., 1990).

Dense blue staining was observed throughout the longitudinal and circumferential layers of SMCs within the wall of the ureter. In contrast, β-galactosidase activity was not observed within the epithelial cells lining the lumen of the ureter. Following direct injection of AdSM22-lacZ into the bladder mucosa, focal patches of β-gal+ SMCs were observed surrounding the site of injection. In contrast, β-galactosidase activity was not observed within the bladder epithelium. These data demonstrated that AdSM22-lacZ programs transgene-expression in visceral, as well as vascular, SMCs.

The 441-bp murine SM22α promoter is active in embryonic skeletal muscle cells and the somites of transgenic mice (Kim et al., 1997). To determine whether AdSM22-lacZ programs transgene expression in adult skeletal muscle in vivo, $10^9$-PFU of the AdSM22-lacZ virus was injected intramuscularly into the rat rectus abdominus and quadriceps muscles. In contrast to the dense blue staining observed in visceral SMCs following direct injection into the wall of the ureter and bladder, P-galactosidase activity was not observed in either the rectus abdominus or quadriceps muscles. Thus, the lacZ reporter gene encoded by AdSM22-lacZ is expressed exclusively in visceral and vascular SMCs when administered intra-arterially, intravenously, or intramuscularly.

Example 12

Adenovirus Mediated Expression of a Cell Cycle Control Gene

The Rb protein inhibits cell cycle progression in many mammalian cell types (Hollingsworth et al., Curr. Opin. Genet. Dev., 3:55, 1993), and has been shown to be an important regulator of vascular smooth muscle proliferation (Chang et al., 1995a). In its unphosphorylated state, the Rb gene product binds and inactivates certain cellular transcription factors that are required for cell cycle progression (Chen et al., Cell, 58:1193, 1989) and upon phosphorylation, the transcription factors are released and the cell progresses through the proliferation cycle. A gene encoding a phosphorylation deficient Rb gene product has been constructed and shown to constitutively inhibit smooth muscle cell cycle proliferation (Chang et al., 1995a) when transfected into rat aortic smooth muscle cells in a replication defective adenovirus vector. Further, the Chang reference also shows that replication defective adenovirus vectors can be used to express heterologous genes in rat carotid arteries in vivo upon direct exposure of isolated segments of injured artery to the adenovirus. A similar study was done in isolated porcine arteries and again the adenoviral transferred constitutive Rb gene product was shown to be expressed and to inhibit smooth muscle cell proliferation.

In a prophetic example of the present invention, this phosphorylation deficient Rb gene product may also be expressed under the control of the smooth muscle specific promoter contained in an adenovirus vector as disclosed herein, thus directing expression of the Rb gene product specifically in smooth muscle cells. Such administration is contemplated to arrest smooth muscle cell proliferation when the described vector expressing Rb from the SM22α promoter is administered to an animal or human subject as described in the previous examples, particularly following arterial balloon injury. This method of preventing restenosis or other smooth muscle cell proliferative disorders offers the advantage of administration of the virus vector by a less invasive method such as intravenous injection. It is also contemplated that other cell cycle control gene products, such as p53 for example, would be effective in this method of preventing restenosis.

Example 13

Identification of Smooth Muscle Specific Trans-Acting Transcription Factors

Identification of Nuclear Protein Binding Sites in the SM22α Promoter

To identify nuclear protein binding sites within the 441-bp SM22α promoter, DNase I footprint analyses were performed. Three overlapping genomic subfragments (bp −441 to −256, bp −256 to −89, and bp −89 to +41) spanning the 482-bp (bp −441 to +42) SM22α promoter were subjected to DNase I footprint analyses using nuclear extracts from the SMC line, A7r5 (which express high levels of SM22α mRNA) and NIH 3T3 cells. The sense and antisense strands of the three genomic subfragments were end-labeled and incubated in the absence (control) or presence of A7r5 and NIH 3T3 (3T3) of nuclear extracts before partial digestion with DNase I (concentrations varied from 5 U/ml to 22.5 U/ml). Standard Maxam and Gilbert purine (G+A) sequencing reactions were run in parallel. The six protected regions identified on both strands with A7r5 nuclear extracts were designated smooth muscle elements (SME)-1-6, respectively. Two footprinted regions, SME-1 (bp −279 to −256) and SME-4 (bp −171 to −136), contain embedded SREs, or CArG boxes (CCWWWWWWGG, SEQ ID NO:47), that have been shown previously to bind the MADS box transcription factor, SRF, and play an important role in regulating transcription of the genes encoding skeletal and cardiac α-actin (Minty et al., 1986; Moss et al., J. Biol. Chem., 269:12731, 1994; Muscat et al., Gene Exp. 2:111, 1992). Fine differences in the digestion patterns between nuclear extracts prepared from A7r5 and NIH 3T3 cells could be distinguished over the SME4 site. Several studies suggest that nucleotides embedded within and/or flanking CArG boxes regulate binding of ternary complex factors (TCFs), including members of the ets and homeodomain families of transcription factors. Thus, the finding that a PEA3 motif (bp −295 to −289), which has been demonstrated to bind in vitro to ets family members, lies 23-bp 5' of the SME-1 motif is noteworthy. Similarly, SME-4 spans a GGAG motif (bp −142 to bp −139) which has been demonstrated to bind to TCFs in the ets family of transcription factors (Johansen and Prywes, Biochem. Biophys. Acta. 1242:1–10, 1995). Moreover, the SME4 motif contains the embedded motif ATATGG (bp −146 to bp −141) which has been demonstrated to bind homeobox transcription factors including Csx/Nkx2.5 (Chen et al., 1996).

The SME-2 nuclear protein binding site (bp −249 and bp −216) contains consensus binding motifs for the ubiquitously expressed transcription factors, Sp1 (KRGGCKRRK) and AP2 (CCCMNSSS). Fine differences in the digestion patterns between nuclear extracts prepared from A7r5 and NIH 3T3 cells could be distinguished over this site. The SME-3 nuclear protein binding site (bp −215 to bp −186), which is flanked by DNase I hypersensitive sites at both its 5' and 3' borders, was protected only by nuclear extracts prepared from A7r5 and not by extracts prepared from NIH 3T3 cells. This nuclear protein binding site has not been described previously. The SME-5 nuclear protein binding site (bp −86 to bp −66) once again contains consensus Sp1 and AP2 motifs. The SME-6 nuclear protein binding site (bp −59 to −35), lies immediately 5' of the non-consensus TATA box (TTTAA), and contains nucleotide sequences that have been demonstrated previously to bind the cyclic AMP response element (CRE) binding proteins (for review see Lalli and Sassone-Corsi, 1994). An AT-rich sequence (bp −408 to −415) with 8/10 bp sequence identity with the consensus MEF2 binding motif (Gossett et al., 1989) was not protected with either A7r5 or NIH 3T3 nuclear extracts. Taken together, these studies demonstrated six nuclear protein binding sites within the murine SM22α promoter. Three of these binding sites (SME-2, SME-3 and SME-4) demonstrated differential patterns of digestion when incubated with nuclear extracts prepared from A7r5 and NIH 3T3 cells.

Characterization of Trans-Acting Factors that Bind to the SM22α Promoter.

To assess the number, specificity, and identity, of nuclear proteins that bind to the arterial SMC-specific SM22α promoter, a series of electrophoretic mobility shift assays (EMSAs) were performed. To determine whether the SME-1/CArG and SME-4/CArG bind common, overlapping, or distinct, sets of trans-acting factors, EMSAs were performed using radiolabeled SME-1 and SME4 oligonucleotide probes. The radiolabeled SME-1 oligonucleotide probe bound three specific nuclear protein complexes, designated A–C, as determined by addition of specific and non-specific unlabeled competitor oligonucleotides to the binding reactions. Unlabeled SME-4 oligonucleotide competed for binding of complex A, but failed to compete for complexes B and C. Unlabeled Sp1 oligonucleotide competed for binding of complex B (that co-migrated with complex A), as well as, complex C. Antibody supershift studies confirmed that complex A contains SRF (or an antigenically related protein) and complex B contains Sp1 (or an antigenically related protein).

EMSAs performed with the radiolabeled SME-4 oligonucleotide probe demonstrated four specific nuclear protein complexes, designated A–D, as determined by addition of specific and non-specific competitor oligonucleotides. Addition of unlabeled SME-1 oligonucleotide competed only for binding of complexes A and B. Antibody supershift studies revealed that both of these low-mobility nuclear protein complexes contained a protein identical, or antigenically-related, to SRF, while complexes C and D contained a protein identical, or antigenically-related, to YY1. Taken together, these data demonstrate that, as expected, SRF (or an SRF-containing protein complex) binds to both the SME-1 and SME-4 sites. The demonstration of two low mobility SME-4 binding activities containing SRF (complexes A and B) suggests that one, or both, of these complexes may contain additional trans-acting factors. In addition, SME-1 bound Sp1 (complex B) and one potentially novel nuclear protein complex (complex C) that does not bind to SME-4. Conversely, SME-4 binds the ubiquitously expressed and potentially negative regulatory factor, YY1 (Gualberto et al., Mol. Cell. Biol 12:4209, 1992; Lee et al., Proc. Natl. Acad. Sci., USA 89:9814, 1992; Lee et al., Oncogene 9:1047, 1994) (complexes C and D), while SME-1 does not.

Both the SME-2 and SME-5 sites are GC-rich motifs that contain potential Sp1 and AP2 motifs. EMSAs performed with nuclear extracts prepared from primary rat aortic SMCs and radiolabeled oligonucleotides corresponding to the SME-2 and SME-5 nuclear protein binding sites, respectively, revealed identical band-shift patterns suggesting that these two motifs might bind a common set of trans-acting factors. Each probe bound three specific nuclear protein complexes, designated A–C, as determined by addition of unlabeled specific and non-specific oligonucleotide competitors. Unlabeled SME-2 oligonucleotide competed for binding of each nuclear protein complex that bound the radiolabeled SME-5 probe and visa versa. Moreover, an oligonucleotide containing a consensus Sp1 motif competed for binding of complexes A–C. Antibody supershift studies revealed that complex A was ablated and supershifted by pre-incubation with Sp1-specific antiserum, but not by control murine IgG, or α-AP2 antiserum. Each of these nuclear protein complexes were also present in nuclear extracts prepared from non-SMC lineages including the lymphoid lines, WEHI and 70Z/3. These data demonstrate that the SME-2 and SME-5 nuclear protein binding sites each bind three ubiquitously expressed nuclear protein complexes, at least one of which contains a protein that is identical, or antigenically related, to Sp1.

As discussed above, SME-3 was protected from DNase I digestion by nuclear extracts prepared from A7r5 cells, but not by extracts prepared from NIH 3T3 cells, suggesting that this previously undescribed motif might bind one or more SMC lineage-specific trans-acting factors. EMSAs performed with the radiolabeled SME-3 oligonucleotide probe revealed three specific binding activities, designated A–C, as determined by addition specific and non-specific competitor oligonucleotides. Antibody supershift studies revealed that complex B and C contained YY1 (or an antigenically related protein). None of the nuclear protein complexes were supershifted by control IgG or α-Sp1 antiserum. To determine whether any of these nuclear protein complexes were expressed in a lineage-restricted fashion, EMSAs were performed with the SME-3 probe and nuclear extracts prepared from primary rat aortic SMCs, the SMC line, A7r5, C3H10T1/2 and NIH 3T3 fibroblasts, and the mouse T cell line, EL4. Interestingly, complex C, which was ablated by pre-incubation with a-YY1 antiserum, was present only in primary rat aortic SMCs and the SMC line A7r5, but was absent in C3H10T1/2, NIH 3T3, and EL4 nuclear extracts. Moreover, three faint complexes were identified in C3H10T1/2, NIH 3T3 and EL4 cells, but were not present in SMC extracts. Taken together, these data suggest that the SME-3 nuclear protein binding site, a motif which has not been described previously, binds YY1 and one or more, as yet, unidentified SMC-specific and/or lineage restricted trans-acting factors. In addition, the radiolabeled SME-3 probe binds three nuclear protein complexes that are present in several non-SMC lines, but not in primary vascular SMCs or the SMC line, A7r5.

EMSAs performed with a radiolabeled oligonucleotide corresponding to the SME-6 nuclear protein binding site revealed four specific nuclear protein complexes, designated A–D, respectively. Each of these complexes were competed with unlabeled SME-6 oligonucleotide. Moreover, addition of an unlabeled consensus CRE oligonucleotide derived from the T cell receptor a enhancer competed exclusively for binding of complexes B and C. Pre-incubation of the binding reactions with α-CREB-1 antiserun ablated and supershifted complex B, while complex C was ablated by addition of α-ATF-1 antiserum. In addition, complex A was ablated and supershifted by pre-incubation with α-Sp1 antiserum. Finally, complex D was ablated by the addition of α-YY1 antiserum. In contrast, none of the four complexes were ablated or supershifted following pre-incubation with control rabbit or murine IgG, or antisera that recognize GATA-4 or SRF. Interestingly, EMSAs performed with the radiolabeled SME-6 oligonucleotide probe and nuclear extracts prepared from the non-SMC lines, C2C12 myotubes, C3H10T1/2 and NIH 3T3 fibroblasts, and EL4 T cells, revealed fine differences in the mobilities of several nuclear protein complexes (and/or novel complexes), as well as, increased intensity in each of the SME-6 binding activities. Taken together, these data revealed that the SME-6 motif binds CREB-1 and ATF-1, each of which are expressed in primary vascular SMCs, as well as, the ubiquitously expressed transcription factors, Sp1 and YY1.

Figure 2:
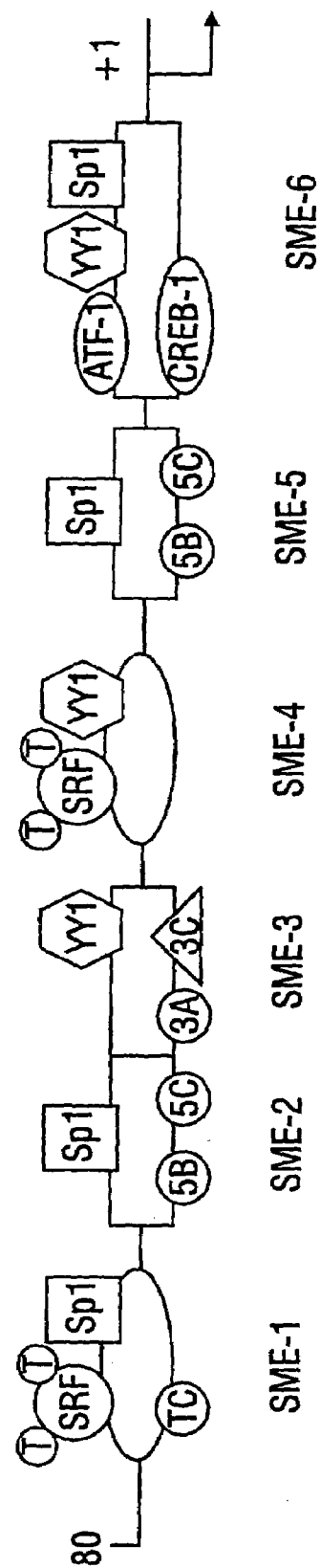
FIG. 2 Schematic representation of the cis-acting elements and the trans-acting factors identified by DNase I footprint and EMSAs analyses that bind to the SM22α promoter. Six nuclear protein binding sites were identified by DNase I footprint analysis in the 441-bp arterial SMC-specific SM22α promoter that were designated SME-1-6, respectively. Trans-acting factors identified by EMSA that bind to each nuclear protein binding site are shown above or below each cis-acting element. Binding sites for SRF and ternary complex factors (T) (SME-1 and SME-4), Sp1 (SME-1, -2, -5, -6), YY1 (SME-3, -4, -6), CREB-1 (SME-6) and ATF−1 (SME-6) were identified. Nuclear protein complexes that could not be positively identified by antibody supershift reactions are shown in gray below the nuclear protein binding site to which they bind.

In summary, as shown in FIG. 2, the arterial SMC-specific SM22α promoter contains six nuclear protein binding sites, designated smooth muscle element (SME)1-6, respectively. SME-1/CArG binds SRF (and ternary complex factors), Sp1 and one unidentified nuclear protein complex that is not cross-competed by SME-4/CArG oligonucleotides. SME-2 binds three specific nuclear protein complexes at least one of which contains Sp1, each of which also binds to the SME-5 site. SME-3, a motif that has not been described previously, binds YY1 and two unidentified nuclear protein complexes, one of which includes a potentially novel lineage-restricted trans-acting factor. In addition, the SME-3 motif binds several trans-acting factors which are present in nuclear extracts prepared from non-SMCs but which are not present in SMC extracts. SME4/CArG binds nuclear protein complexes containing SRF and YY1-related proteins. Two high mobility complexes were ablated and supershifted by pre-incubation with a-SRF antiserum suggesting that one, or both, of these nuclear protein complexes may contain accessory factors. Finally, SME-6 binds CREB-1, ATF-1, YY1, and Sp1.

Example 14

Functional characterization of the SM22α Promoter

To characterize the functional significance of each of the cis-acting elements within the SM22α promoter, specific mutations that abolish nuclear binding of one or more trans-acting factors to nuclear protein binding sites located within the SM22α promoter were created within the context of the p-441SM22luc reporter plasmid. The effect of each mutation was assessed by transient transfection analysis of each mutant SM22α promoter luciferase reporter plasmid into primary rat aortic SMCs. To assess the function of the SME-1/CArG and SME-4/CArG sites, each of which bind SRF, mutations were created that abolish SRF binding to SME-1, and SRF and YY1 binding to SME-4, respectively. These mutations did not affect binding of any other nuclear protein complex (demonstrated by EMSA) to SME-1 or SME-4. Transfection analyses revealed that mutation of the SME-1 site resulted in a 55% reduction in normalized luciferase activity compared to that obtained with the p-441 SM22luc plasmid. Remarkably, a two nucleotide substitution in the SME-4 site that abolished SRF binding activity resulted in a 88% reduction in normalized luciferase activity compared to that obtained with the wild type SM22α promoter. Moreover, the p-441SM22µCArG plasmid, which contains mutations in both SME-1 and 4 that inhibit binding of SRF, completely abolished transcriptional activity of the SM22α promoter in primary rat aortic SMCs and the SMC-line A7r5. These data demonstrate that the SME-1 and -4 nuclear protein binding sites are required for activity of the SM22α promoter in arterial SMCs in vitro. Moreover, these data suggest that SM22α promoter activity is critically-dependent upon the SME-4 site, SRF, and/or trans-acting factors that interact with SRF.

To assess the functional significance of each of the other (non-CArG containing) nuclear protein binding sites in the SM22α promoter, mutations that abolish binding of one or more trans-acting factor to each site were created within the context of the 441-bp SM22α promoter containing plasmid, p-441SM22luc. Because the SME-2 and SME-5 nuclear protein binding sites, each bind a nuclear protein complex containing Sp1, in addition to two other common nuclear protein complexes, mutations were created within the context of the p-441 SM22-luc plasmid that abolish binding of each trans-acting factor to SME-2, SME-5, and both SME-2 and SME-5. Transfection of each of these plasmids and the p-441SM22-luc into primary rat aortic SMCs demonstrated that mutation of the SME-2, SME-5, and SME-2 and SME-5, resulted in 58%, 6% and 70% respective reductions in normalized luciferase activities. These data suggest that within the context of the SM22α promoter, the SME-2, and -5 nuclear protein binding sites are required for full promoter activity, but may be functionally redundant.

Mutation in the SME-3 site which abolishes binding of all three SME-3 binding activities (including the potentially novel lineage-restricted trans-acting factor) resulted in a 50% reduction in transcriptional activity compared to that observed with the native SM22α promoter. These data suggest either that activity of the SM22α promoter in arterial SMCs is not critically dependent on this potentially novel lineage-restricted trans-acting factor, or alternatively, that an additional nuclear protein binding site for this lineage-restricted trans-acting factor exists in the 441-bp SM22α promoter (that was not detected by DNase I footprint analyses and EMSAs). To assess the functional significance of the SME-6 nuclear protein binding site, and to determine whether the CRE located within SME-6 is required for promoter activity, the −441 SM22μCREB/SME-6 plasmid, which abolishes binding specifically of each of the CRE-related complexes (but not YY1) was compared to the p-441SM22luc reporter plasmid. The single mutation within the CREB motif reduced transcriptional activity by approximately 60%. In contrast, mutations within SME-6 that do not abolish CRE binding activities did not significantly decrease transcriptional activities. These data suggest that CREB family members may play an important functional role in transcription of the SM22α gene in VSMCs.

The Arterial SMC-Specific SM22α Promoter is CArG-Dependent In Vivo

As shown above, mutations of the SME-1/CArG and SME-4/CArG elements that inhibited binding of SRF to the SM22α promoter, totally abolished SM22α promoter activity in arterial SMCs in vitro. To determine whether SME-1 and 4 are required for activity of the SM22α promoter in arterial SMCs (and the myotomal component of the somites) in vivo, transgenic mice were produced containing a transgene, designated −441SM22μCArG, that encodes the bacterial lacZ reporter gene under the transcriptional control of a mutant SM22α promoter containing mutations in both SME-1 and SME-4 that abolish binding of SRF (as described above). Thirteen independent −441SM22μCArG transgenic lines were produced with copy numbers ranging between 1 and 730 copies per cell. In contrast to the −441SM221acZ transgenic mice that expressed the lacZ transgene in the arterial SMCs and within the myotomal component of the somites, in 12 out of 13 independent −441SM22μCArG lines, β-galactosidase activity could not be detected in either the arterial SMCs or within the myotomal component of the somites at ED11.5. In one line harboring the −441SM22μCArG transgene (that contained 5 copies per cell), blue staining was detected exclusively within the cardiac outflow tract, but not within the SMCs of the dorsal aorta or branch arteries, the somites, or any other tissue. Given the low frequency at which this pattern of lacZ expression was observed, it is likely that it resulted from integration of the transgene near a cryptic enhancer element. These data demonstrate that the SME-1 and SME-4 nuclear protein binding sites located within arterial SMC-specific SM22α promoter are required for SM22α promoter activity in vivo. Moreover, these data suggest strongly that SRF plays an important role in regulating activity of the SM22α promoter in vivo.

While the compositions and methods of this invention have been described in terms of preferred embodiments, it will be apparent to those of skill in the art that variations may be applied to the composition, methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

---

The invention claimed is:

1. A method of inhibiting smooth muscle cell proliferation comprising the steps of:
   (a) obtaining an isolated nucleic acid segment comprising a cell cycle regulatory gene operatively linked to an SM22α promoter region comprising 50 contiguous bases of SEQ ID NO:1 in the region upstream of the transcriptional start site;
   (b) transferring said nucleic acid segment into a smooth muscle cell; and
   (c) maintaining said smooth muscle cell under conditions effective to express said cell cycle regulatory gene; wherein expression of said cell cycle regulatory gene inhibits proliferation of said smooth muscle cell.

2. The method of claim 1, wherein said smooth muscle cell is in an animal.

3. The method of claim 1, wherein said cell cycle regulatory gene operatively linked to an SM22α promoter region is in a viral or plasmid vector.

4. The method of claim 3, wherein said viral vector is an adenoviral vector.

5. The method of claim 1, wherein said cell cycle regulatory gene is selected from the group consisting of Rb, a phosphorylation deficient Rb gene, p53, p21, p16, p27, a cell cycle dependent kinase inhibitor, E2F inhibitor, a CDK kinase or a cyclin gene.

6. A method of inhibiting smooth muscle proliferation comprising the steps of:
   (a) obtaining a nucleic acid segment comprising a cell cycle regulatory gene operatively linked to an SM22α promoter region comprising 50 contiguous bases of SEQ ID NO:1 in the region upstream of the transcriptional start site;
   (b) transferring said nucleic acid segment into a primary smooth muscle cell ex vivo to obtain a transfected cell;
   (c) seeding a bioprosthetic graft or stent with said transfected cell to obtain a seeded graft or stent; and
   (d) placing the seeded graft or stent into a coronary or peripheral artery or vein of a subject;
wherein expression of said cell cycle regulatory gene inhibits proliferation of a smooth muscle cell.

7. The method of claim 1, wherein the SM22α promoter region comprises 100 contiguous bases of SEQ ID NO:1 in the region upstream of the transcriptional start site.

8. The method of claim 1, wherein the SM22α promoter region comprises 500 contiguous bases of SEQ ID NO:1 in the region upstream of the transcriptional start site.

9. The method of claim 1, wherein the SM22α promoter region comprises the entire region upstream of the transcriptional start site in SEQ ID NO:1.

10. The method of claim 6, wherein the SM22α promoter region comprises 100 contiguous bases of SEQ ID NO:1 in the region upstream of the transcriptional start site.

11. The method of claim 6, wherein the SM22α promoter region comprises 500 contiguous bases of SEQ ID NO:1 in the region upstream of the transcriptional start site.

12. The method of claim 6, wherein the SM22α promoter region comprises the entire region upstream of the transcriptional start site in SEQ ID NO:1.

* * * * *

UNITED STATES PATENT AND TRADEMARK OFFICE
CERTIFICATE OF CORRECTION

| | |
|---|---|
| PATENT NO. | : 7,169,764 B1 |
| APPLICATION NO. | : 09/381750 |
| DATED | : January 30, 2007 |
| INVENTOR(S) | : Parmacek et al. |

It is certified that error appears in the above-identified patent and that said Letters Patent is hereby corrected as shown below:

Title page, item [63], line 1, insert -- This application is a national phase application under 35 U.S.C. § 371 of International Application No. PCT/US97/16204 filed August 29, 1997, which claims priority to U.S. Patent Application Serial No. 09/380,928, filed September 9, 1999, now abandoned, and to U.S. Patent Application Serial No. 08/726,807, filed October 7, 1996, now U.S. Patent 6,090,618, which claims priority to U.S. Application Ser. No. 60/004,868, filed on October 5, 1995, now abandoned. -- therefor.

In column 1, line 9, after "which claims priority to", insert -- U.S. Patent Application Serial No. 09/380,928, filed September 9, 1999, now abandoned, and --therefor.

Signed and Sealed this

Fourteenth Day of August, 2007

JON W. DUDAS
*Director of the United States Patent and Trademark Office*